(12) United States Patent
Glasgow et al.

(10) Patent No.: US 11,574,540 B2
(45) Date of Patent: *Feb. 7, 2023

(54) TRAFFIC DISRUPTION DETECTION USING PASSIVE MONITORING OF VEHICLE OCCUPANT FRUSTRATION LEVEL

(71) Applicant: eBay Inc., San Jose, CA (US)

(72) Inventors: Dane Glasgow, Los Altos, CA (US); Matthew Bret MacLaurin, Santa Cruz, CA (US); Neville Rhys Newey, Pleasanton, CA (US); Justin VanWinkle, San Jose, CA (US); Christopher Michael Hall, San Jose, CA (US); Trista Mcneill, San Jose, CA (US); David Ramadge, San Jose, CA (US)

(73) Assignee: eBay Inc., San Jose, CA (US)

( * ) Notice: Subject to any disclaimer, the term of this patent is extended or adjusted under 35 U.S.C. 154(b) by 265 days.

This patent is subject to a terminal disclaimer.

(21) Appl. No.: 17/130,675

(22) Filed: Dec. 22, 2020

(65) Prior Publication Data

US 2021/0125495 A1 Apr. 29, 2021

Related U.S. Application Data

(63) Continuation of application No. 15/726,056, filed on Oct. 5, 2017, now Pat. No. 10,909,846, which is a
(Continued)

(51) Int. Cl.
*G08G 1/09* (2006.01)
*G08G 1/01* (2006.01)
(Continued)

(52) U.S. Cl.
CPC ........... *G08G 1/093* (2013.01); *A61B 5/0205* (2013.01); *A61B 5/1118* (2013.01); *A61B 5/165* (2013.01);
(Continued)

(58) Field of Classification Search
CPC ...... G08G 1/093; G08G 1/012; G08G 1/0125; G08G 1/0133; G08G 1/0141;
(Continued)

(56) References Cited

U.S. PATENT DOCUMENTS

| 6,898,569 B1 | 5/2005 | Bansal et al. |
| 7,375,652 B2 | 5/2008 | Reeves et al. |

(Continued)

FOREIGN PATENT DOCUMENTS

| CN | 102538810 A | 7/2012 |
| CN | 102881199 A | 1/2013 |

(Continued)

OTHER PUBLICATIONS

Notice Of Allowance received for U.S. Appl. No. 15/726,056, dated Dec. 4, 2020, 5 pages.

(Continued)

*Primary Examiner* — Richard M Camby
(74) *Attorney, Agent, or Firm* — FIG. 1 Patents

(57) ABSTRACT

Aspects of the present disclosure include a navigation system and computer-implemented methods for detecting traffic disruption events based on an analysis of input component data obtained from navigation-enabled devices of vehicles near a particular location. Traffic disruption events are events such as accidents, construction road closures, police and speed traps, or road hazards that cause a decrease in the flow of traffic along a particular route and thus, added time delays for occupants of vehicles traveling along those routes. The navigation system scores the input component data associated with each vehicle and aggregates the scored input component data to obtain a frustration score associated with the vehicle. The navigation system may detect traffic (Continued)

disruption events based on a number of vehicles near a particular area having associated frustration scores above a certain threshold.

20 Claims, 18 Drawing Sheets

Related U.S. Application Data continuation of application No. 14/982,945, filed on Dec. 29, 2015, now Pat. No. 9,792,814.

(51) Int. Cl.
| | |
|---|---|
| G08G 1/0969 | (2006.01) |
| A61B 5/0205 | (2006.01) |
| A61B 5/00 | (2006.01) |
| G01C 21/32 | (2006.01) |
| G08G 1/0968 | (2006.01) |
| A61B 5/16 | (2006.01) |
| A61B 5/11 | (2006.01) |
| A61B 5/18 | (2006.01) |
| G01C 21/36 | (2006.01) |
| A61B 5/024 | (2006.01) |
| G01C 21/34 | (2006.01) |

(52) U.S. Cl.
CPC .............. *A61B 5/18* (2013.01); *A61B 5/6893* (2013.01); *G01C 21/32* (2013.01); *G01C 21/3691* (2013.01); *G08G 1/012* (2013.01); *G08G 1/0125* (2013.01); *G08G 1/0133* (2013.01); *G08G 1/0141* (2013.01); *G08G 1/0969* (2013.01); *G08G 1/096816* (2013.01); *G08G 1/096844* (2013.01); *G08G 1/096866* (2013.01); *G08G 1/096883* (2013.01); *A61B 5/024* (2013.01); *A61B 5/11* (2013.01); *A61B 2562/0204* (2013.01); *G01C 21/3415* (2013.01)

(58) Field of Classification Search
CPC ....... G08G 1/096816; G08G 1/096844; G08G 1/096866; G08G 1/096883; G08G 1/0969; A61B 5/0205; A61B 5/1118; A61B 5/165; A61B 5/18; A61B 5/6893; A61B 5/024; A61B 5/11; A61B 2562/0204; G01C 21/32; G01C 21/3691; G01C 21/3415
See application file for complete search history.

(56) References Cited

U.S. PATENT DOCUMENTS

| | | | |
|---|---|---|---|
| 7,493,208 B1 | 2/2009 | Craine | |
| 8,024,111 B1 | 9/2011 | Meadows et al. | |
| 8,289,188 B2 | 10/2012 | Ueno et al. | |
| 8,364,395 B2 | 1/2013 | French et al. | |
| 8,850,597 B1 | 9/2014 | Gates et al. | |
| 8,855,903 B2 | 10/2014 | Chiu | |
| 9,123,035 B2 | 9/2015 | Penilla et al. | |
| 9,229,905 B1 | 1/2016 | Penilla et al. | |
| 9,285,944 B1 | 3/2016 | Penilla et al. | |
| 9,467,515 B1 | 10/2016 | Penilla et al. | |
| 9,709,417 B1 | 7/2017 | Glasgow et al. | |
| 9,792,814 B2 * | 10/2017 | Glasgow | G08G 1/093 |
| 9,989,369 B2 | 6/2018 | Glasgow et al. | |
| 10,281,292 B2 | 5/2019 | Glasgow et al. | |
| 10,768,009 B2 * | 9/2020 | Glasgow | G01C 21/3617 |
| 10,909,846 B2 * | 2/2021 | Glasgow | G01C 21/3691 |
| 10,914,598 B2 | 2/2021 | Glasgow et al. | |
| 11,326,896 B2 * | 5/2022 | Glasgow | G08G 1/096844 |
| 2002/0052689 A1 | 5/2002 | Yamashita et al. | |
| 2008/0091341 A1 | 4/2008 | Panabaker et al. | |
| 2009/0124863 A1 | 5/2009 | Liu et al. | |
| 2009/0287408 A1 | 11/2009 | Gerdes et al. | |
| 2010/0036602 A1 | 2/2010 | Lee | |
| 2011/0015468 A1 | 1/2011 | Aarts et al. | |
| 2011/0208646 A1 | 8/2011 | Mcmaster et al. | |
| 2012/0078509 A1 | 3/2012 | Choi | |
| 2012/0289788 A1 | 11/2012 | Jain et al. | |
| 2012/0289789 A1 | 11/2012 | Jain et al. | |
| 2013/0132854 A1 | 5/2013 | Raleigh et al. | |
| 2013/0147820 A1 | 6/2013 | Kalai et al. | |
| 2014/0142852 A1 | 5/2014 | Vertelney et al. | |
| 2014/0229255 A1 | 8/2014 | Scofield et al. | |
| 2014/0236472 A1 | 8/2014 | Rosario | |
| 2014/0309933 A1 | 10/2014 | Shin et al. | |
| 2015/0112159 A1 | 4/2015 | He et al. | |
| 2015/0253144 A1 | 9/2015 | Rau et al. | |
| 2015/0260532 A1 | 9/2015 | Sanio et al. | |
| 2015/0292893 A1 | 10/2015 | Bartsch et al. | |
| 2015/0319093 A1 | 11/2015 | Stolfus | |
| 2016/0104486 A1 | 4/2016 | Penilla et al. | |
| 2016/0110997 A1 | 4/2016 | Ur et al. | |
| 2017/0011559 A1 | 1/2017 | Graham et al. | |
| 2017/0184409 A1 | 6/2017 | Glasgow et al. | |
| 2017/0184411 A1 | 6/2017 | Glasgow et al. | |
| 2017/0186315 A1 | 6/2017 | Glasgow et al. | |
| 2017/0314953 A1 | 11/2017 | Glasgow et al. | |
| 2018/0033299 A1 | 2/2018 | Glasgow et al. | |
| 2018/0245932 A1 | 8/2018 | Glasgow et al. | |
| 2018/0303396 A1 | 10/2018 | Wild | |
| 2019/0204107 A1 | 7/2019 | Glasgow et al. | |
| 2020/0309559 A1 | 10/2020 | Glasgow | |
| 2021/0033409 A1 | 2/2021 | Glasgow et al. | |

FOREIGN PATENT DOCUMENTS

| | | |
|---|---|---|
| CN | 104182496 A | 12/2014 |
| CN | 108474662 A | 8/2018 |
| DE | 10224466 A1 | 12/2003 |
| EP | 1202030 A2 | 5/2002 |
| EP | 1202030 B1 | 4/2006 |
| EP | 3397925 A1 | 11/2018 |
| JP | 2006023252 A | 1/2006 |
| KR | 1020070019675 A | 2/2007 |
| KR | 100811631 B1 | 3/2008 |
| TW | 201007130 A | 2/2010 |
| WO | 2017117250 A1 | 7/2017 |

OTHER PUBLICATIONS

Office Action Received for Chinese Patent Application No. 201680076908.8, dated Jan. 29, 2021, 8 Pages (only official copy).
Corrected Notice Of Allowability received for U.S. Appl. No. 15/726,056, dated Dec. 28, 2020, 3 Pages.
Final Office Action Received for U.S. Appl. No. 15/726,056, dated Jul. 13, 2020, 28 Pages.
First Action Interview Office Action Summary Received for U.S. Appl. No. 15/726,056 dated Nov. 18, 2019, 4 pages.
First Action Interview Pre-Interview Communication received for U.S. Appl. No. 15/726,056, dated Jul. 30, 2019, 4 pages.
Non-Final Office Action Received for U.S. Appl. No. 15/726,056, dated Nov. 13, 2020, 5 pages.
International Written Opinion received for PCT Patent Application No. PCT/US2016/068937, dated Mar. 17, 2017, 5 pages.
Notice Of Allowance received for Korean Patent Application No. 10-2018-7018482, dated Feb. 6, 2020, 4 pages(3 Pages Of Official Copy & 1 page of English Translation ).
Office Action received for Korean Patent Application No. 10-2018-7018482, dated Aug. 13, 2019, 14 pages.
First Action Interview-Pre-Interview Communication received for U.S. Appl. No. 14/982,945 dated Apr. 7, 2017, 4 pages.
Notice of Allowance Received for U.S. Appl. No. 14/982,945, dated Jun. 14, 2017, 9 pages.
Supplemental Notice of Allowability received for U.S. Appl. No. 14/982,945, dated Sep. 21, 2017, 2 pages.

(56) References Cited

OTHER PUBLICATIONS

Notice of Allowance received for U.S. Appl. No. 14/983,000, dated Mar. 16, 2017, 9 Pages.
Supplemental Notice of Allowability received for U.S. Appl. No. 14/983,000, dated Jun. 2, 2017, 2 pages.
Corrected Notice of Allowability received for U.S. Appl. No. 14/983,261, dated May 3, 2018, 2 pages.
Corrected Notice of Allowability received for U.S. Appl. No. 14/983,261, dated May 2, 2018, 2 pages.
International Search Report received for PCT Patent Application No. PCT/US2016/068937, dated Mar. 17, 2017, 2 pages.
Notice of Allowance received for U.S. Appl. No. 14/983,261 dated Jan. 26, 2018, 8 Pages.
Preinterview First Office Action received for U.S. Appl. No. 14/983,261 dated Jul. 7, 2017, 5 Pages.
First Action Interview Pre-Interview Communication received for U.S. Appl. No. 15/651,658, dated Oct. 16, 2018, 3 pages.
Notice of Allowance received for U.S. Appl. No. 15/651,658, dated Jan. 23, 2019, 7 pages.
Supplemental Notice of Allowance Received For U.S. Appl. No. 15/651,658, dated Feb. 12, 2019, 2 pages.
International Preliminary Report on Patentability received for PCT Application No. PCT/US2016/068937, dated Jul. 12, 2018, 7 pages.
Extended European Search Report received for European Patent Application No. 16882580.0, dated Dec. 7, 2018, 9 pages.
Supplemental Notice Of Allowability received for U.S. Appl. No. 16/352,658, dated Aug. 13, 2020, 2 pages.
Notice Of Allowance received for U.S. Appl. No. 16/352,658, dated May 5, 2020, 5 pages.
Non Final Office Action Received for U.S. Appl. No. 16/352,658, dated Jan. 22, 2020, 7 pages.
Final Office Action Received for U.S. Appl. No. 16/352,658, dated Apr. 8, 2020, 6 pages.
Advisory Action received for U.S. Appl. No. 15/965,630, dated Dec. 17, 2019, 5 pages.
Corrected Notice Of Allowability received for U.S. Appl. No. 15/965,630, dated Dec. 9, 2020, 2 pages.
Corrected Notice Of Allowability received for U.S. Appl. No. 15/965,630, dated Sep. 30, 2020, 3 Pages.
Corrected Notice Of Allowability received for U.S. Appl. No. 15/965,630, dated Oct. 9, 2020, 3 Pages.
Final Office Action Received for U.S. Appl. No. 15/965,630, dated Oct. 4, 2019, 12 pages.
Non Final Office Action Received for U.S. Appl. No. 15/965,630, dated Jun. 26, 2020, 11 pages.
Non-Final Office Action received for U.S. Appl. No. 15/965,630, dated Jun. 28, 2019, 11 pages.
Notice Of Allowance received for U.S. Appl. No. 15/965,630, dated Aug. 27, 2020, 9 Pages.
Restriction Requirement received for U.S. Appl. No. 15/965,630 dated Mar. 28, 2019, 6 pages.
First Action Interview-Office Action Summary received for U.S. Appl. No. 14/983,261, dated Oct. 19, 2017, 6 pages.
Non Final Office Action received for U.S. Appl. No. 16/903,195, dated Nov. 16, 2021, 7 pages.
Notice of Allowance received for U.S. Appl. No. 16/903,195, dated Feb. 3, 2022, 5 pages.
Decision of Rejection received for Chinese Patent Application No. 201680076908.8, dated Jan. 7, 2022, 10 pages (2 pages of English translation and 8 pages of official copy).
U.S. Appl. No. 16/903,195 , "Supplemental Notice of Allowability Received for U.S. Appl. No. 16/903,195, dated Feb. 24, 2022", dated Feb. 24, 2022, 2 Pages.
U.S. Appl. No. 62/185,578, "Methods and Systems for Communicating Content to Connected Vehicle Users Based Detected Tone/Mood in Voice Input", Jun. 27, 2015, 99 Pages.
Communication Pursuant To Article 94(3) EPC received for European Patent Application No. 16882580.0, dated Jun. 9, 2021, 9 Pages.
Office Action received for Chinese Patent Application No. 201680076908.8, dated Jun. 17, 2021, 8 pages (1 Page of English translation & 7 Pages of Official Copy).

\* cited by examiner

TRAFFIC DISRUPTION DETECTION USING PASSIVE MONITORING OF VEHICLE OCCUPANT FRUSTRATION LEVEL

PRIORITY

This application is a continuation of and claims the benefit of priority to U.S. patent application Ser. No. 15/726,056, filed on Oct. 5, 2017 entitled "TRAFFIC DISRUPTION DETECTION USING PASSIVE MONITORING OF VEHICLE OCCUPANT FRUSTRATION LEVEL which is a Continuation of U.S. patent application Ser. No. 14/982,945, entitled "TRAFFIC DISRUPTION DETECTION USING PASSIVE MONITORING OF VEHICLE OCCUPANT FRUSTRATION LEVEL," filed on Dec. 29, 2015, which is hereby incorporated by reference herein in its entirety.

TECHNICAL FIELD

This subject matter disclosed herein generally relates to navigation systems. In particular, example embodiments relate to traffic disruption detection based vehicle occupant frustration levels determined through passive monitoring of input components of in-vehicle devices.

BACKGROUND

Modern navigation systems provide users with possible routes to their intended destinations and, in many cases, can suggest certain optimal routes such as the route with the shortest distance or the route that will take the least time in light of traffic considerations. A drawback of these modern navigation systems is that the widespread proliferation of their use results in a large number of vehicles travelling along the same paths, which results in heavy traffic congestion along those paths. Further, once traffic flow slows down on primary paths such as highways, other secondary paths such as surface streets also end up becoming congested with traffic because the navigation systems end up routing subsequent vehicles along those paths. This sort of reactionary re-routing results in inefficient load balancing of traffic, and thus, additional delays for occupants in vehicles trying to reach their intended destinations.

To aid vehicles and their occupants in avoiding heavy traffic, some navigation services allow users to manually report location specific traffic disruptions such as accidents, construction, road closures, police speed traps, and other traffic causing incidents, which are, in turn, provided to other users. However, allowing users to generate reports frequently leads to inaccurate information because of incidental error or intentional deception. Moreover, allowing users to generate reports of these sorts often leads to duplicate reports, which leads to overutilization of computational resources, and as a result, the performance of the navigation service is compromised.

BRIEF DESCRIPTION OF THE DRAWINGS

Various ones of the appended drawings merely illustrate example embodiments of the present disclosure and are not intended to limit its scope to the illustrated embodiments. On the contrary, these examples are intended to cover alternatives, modifications, and equivalents as may be included within the scope of the disclosure.

DETAILED DESCRIPTION

Figure 1:
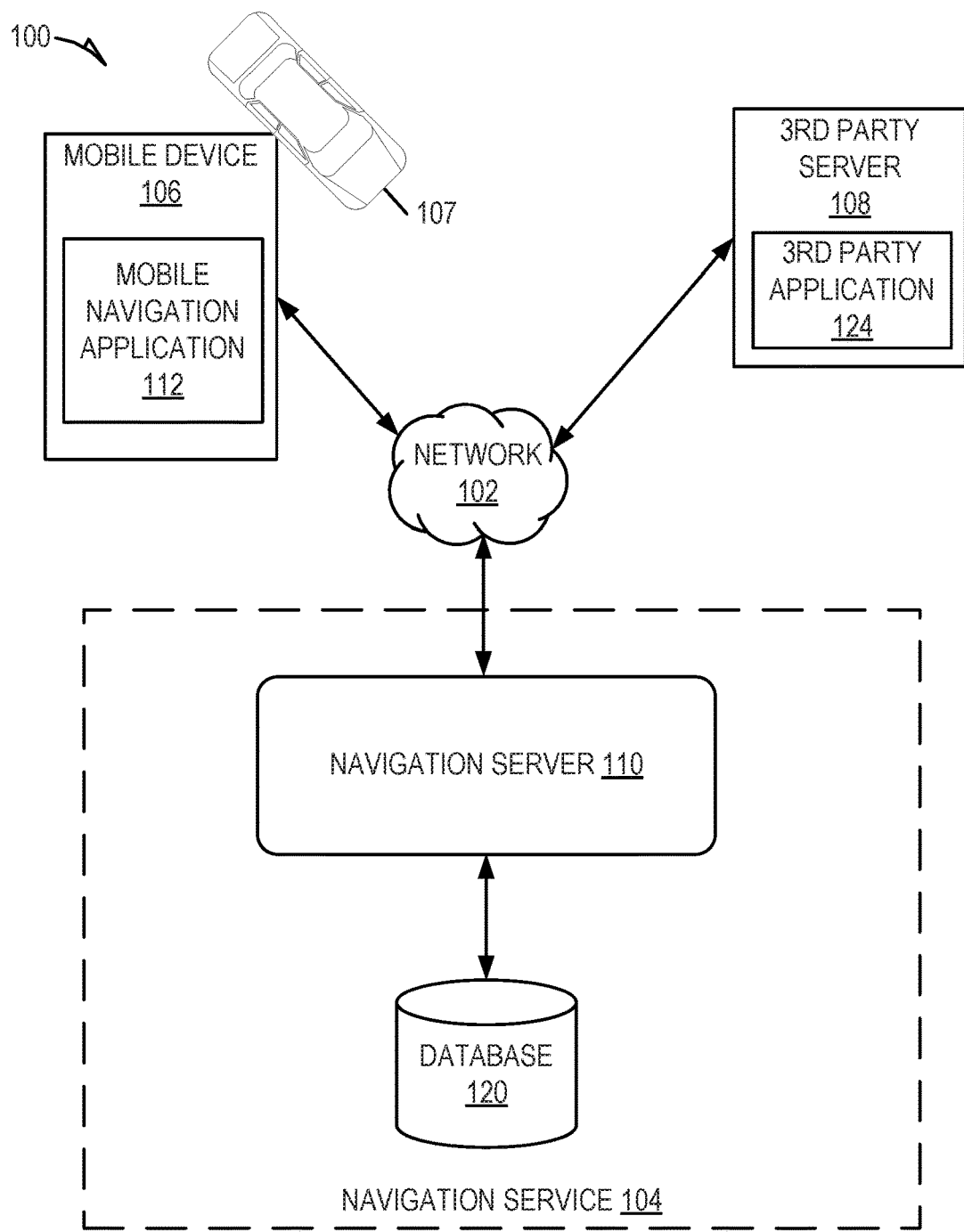
FIG. 1 is a network diagram illustrating a navigation system having a client-server architecture configured for exchanging data over a network with a navigation service, according to example embodiments.

Reference will now be made in detail to specific example embodiments for carrying out the inventive subject matter of the present disclosure. In the following description, specific details are set forth in order to provide a thorough understanding of the subject matter. It shall be appreciated that embodiments may be practiced without some or all of these specific details.

Aspects of the present disclosure relate to a network-based navigation system including a navigation-enabled device in communication with a navigation server over a network. The navigation server forms part of a navigation service that provides various navigation functions to its users (e.g., human users). Users of the navigation service may include occupants of both manned (e.g., human driven) vehicles and unmanned, autonomous (e.g., machine driven) vehicles. Accordingly, it shall be appreciated that the subject matter of the present disclosure is not limited to manned (e.g., human driven) vehicles, and may, in some embodiments, find application in unmanned, autonomous vehicles.

In example embodiments, the navigation system seeks to reduce traffic flow along primary navigation routes (e.g., routes with relatively short travel times) by proactively re-routing vehicles to alternative navigation routes (e.g., routes with relatively longer travel times). The navigation system may re-route vehicles by providing the alternative routes to navigation-enabled devices contained in the vehicles (e.g., either embedded in the vehicle itself or carried by a vehicle occupant). Upon detecting the vehicles traveling along alternative routes (e.g., using location information provided by the navigation-enabled device contained in the vehicles), the navigation system transfers an amount of value (e.g., currency or reward points) to user accounts of occupants of such vehicles. The amount of value provided to occupants of vehicles traveling along the alternative routes are obtained from occupants of other vehicles that are traveling along the primary route. In this way, the navigation system incentivizes vehicle occupants to direct their vehicles to travel along alternative routes instead of primary routes, thereby reducing traffic on primary routes.

Additional example embodiments involve proactively re-routing vehicles based on vehicle occupant frustration levels. More specifically, in some example embodiments, the navigation system provides detour suggestions to navigation-enabled devices based on an analysis of input component data obtained from the navigation-enabled devices. The input component data may, for example, include audio data from a microphone, motion data from a motion sensor, or heart rate data from a heart rate sensor. The navigation system scores the input component data to obtain a measure of frustration (e.g., a feeling of being upset or annoyed) of the user of the navigation-enabled device. Because the user of the navigation-enabled device is an occupant of the vehicle in which the navigation-enabled device resides, the scored input component data is likely to provide a measure of the frustration level of the user as it relates to being in traffic. The navigation system may provide a detour suggestion for display on the navigation-enabled device to persuade the user of the device to direct their vehicle to depart from its current location or route in an effort to remove the vehicle from traffic, and thereby reduce the frustration level of the user. The detour suggestion may include an alternative route to the original destination or an alternative destination. In instances in which the detour suggestion includes an alternative destination, the detour suggestion may further include a monetary incentive such as a coupon that is applicable to a brick-and-mortar retail location corresponding to the alternative destination.

Additional example embodiments involve detecting traffic disruption events based on vehicle occupant frustration levels. More specifically, in some example embodiments, the navigation system identifies traffic disruption events based on an analysis of input component data obtained from navigation-enabled devices of vehicles near a particular location (e.g., vehicles in the same proximity). Traffic disruption events are events such as accidents, construction road closures, police and speed traps, or road hazards that cause a decrease in the flow of traffic along a particular route and thus, added time delays for occupants of vehicles traveling along those routes. The navigation system scores the input component data associated with each vehicle (e.g., input component data obtained from a navigation-enabled device in the vehicle) and aggregates the scored input component data to obtain a frustration score associated with the vehicle. The navigation system may detect traffic disruption events based on a number of vehicles near a particular area having associated frustration scores above a certain threshold. The navigation system may further use the detected traffic disruption events to verify existing user submitted traffic disruption reports by cross-referencing location information associated with each user submitted traffic disruption report.

FIG. 1 is a network diagram depicting a navigation system 100 having a client-server architecture configured for exchanging data over a network 102 with a navigation service 104, according to example embodiments. While the navigation system 100 is depicted as having a client-server architecture, the present inventive subject matter is, of course, not limited to such an architecture, and could equally well find application in an event-driven, distributed, or peer-to-peer architecture system, for example. Further, to avoid obscuring the inventive subject matter with unnecessary detail, various functional components that are not germane to conveying an understanding of the inventive subject matter have been omitted from FIG. 1. Moreover, it shall be appreciated that although the various functional components of the navigation system 100 are discussed in a singular sense, multiple instances of any one of the various functional components may be employed.

As shown, the navigation system 100 includes the navigation service 104 in communication with a mobile device 106 and a third party server 108 over the network 102. The navigation service 104 communicates and exchanges data with entities within the navigation system 100 that pertain to various functions and aspects associated with the navigation system 100 and its users. These data exchanges may include transmitting, receiving (communicating), and processing data to, from, and regarding content and users of the navigation system 100.

The navigation service 104 includes a navigation server 110 to provide server-side functionality, via the network 102 (e.g., the Internet), to client devices such as the mobile device 106. The mobile device 106 may be operated by users, such an occupant of vehicle 107, who use the navigation system 100 to navigate the vehicle 107 to destination locations. The vehicle 107 may be a manned or unmanned, autonomous vehicle, and thus, the vehicle occupant may be a driver or passenger who uses the navigation service to navigate a manned vehicle or passengers of an unmanned autonomous vehicles that utilize the navigation service 104 to provide navigation instructions to an embedded computer system responsible for directing the movement of the unmanned autonomous vehicle. The vehicle 107 is not necessarily a part of the navigation system 100 but is associated with the mobile device 106 as the mobile device 106 may either be embedded in the vehicle 107 or carried by an occupant of the vehicle.

The mobile device 106 may be any sort of navigation-enabled device (e.g., smart phone, tablet computer, or global positioning system (GPS) device) that includes one or more locations components (e.g., GPS components) for determining its location, and a mobile navigation application 112 specifically designed for interacting with the navigation service 104. For example, a vehicle occupant (e.g., a driver or a passenger) may use the mobile navigation application 112 executing on the mobile device 106 to navigate to a destination location using a route provided by the navigation service 104. The mobile navigation application 112 further provides graphical user interfaces (GUIs) that include elements such as maps and directions to aid users in navigating to destination locations. The mobile navigation application 112 may, in some embodiments, when executed by the mobile device 106, configure the mobile device 106 to perform any of the methodologies described herein.

Turning specifically to the navigation service 104, the navigation service 104 includes the navigation server 110 and a database 120. In some embodiments, the navigation service 104 may include an Application Programming Interface (API) server and/or a web server coupled to (e.g., via wired or wireless interfaces) the navigation server 110 to provide programmatic and/or web interfaces respectively to the mobile device 106. The navigation service 104 may, in some embodiments, also include a database server coupled to the navigation server 110 to facilitate access to the database 120. The database 120 may include multiple databases that may be internal or external to the navigation service 104.

The navigation server 110 hosts one or more applications such as a server-side navigation application that provides navigation services to users (e.g., vehicle occupants) who access the navigation service 104. For example, a vehicle occupant may use the mobile navigation application 112 executing on the mobile device 106 to obtain one or more routes to a destination location from the navigation server 110. As a further example, the navigation server 110 may provide data to the mobile device 106 to suggest that the vehicle occupant re-route the vehicle from a primary route to an alternative route. In some instances, the navigation server 110 provides such data based on a frustration level of the vehicle occupant determined from input component data (e.g., sensor data) received from input components (e.g., sensors) embedded in or coupled to the mobile device 106.

The database 120 stores data pertaining to various functions and aspects associated with the navigation system 100 and its users. For example, the database 120 stores maps and routing data to aid in navigation. The database 120 further stores traffic disruption report data including user submitted traffic disruption reports and machine generated traffic disruption reports. The database 120 also stores and maintains user account records for users of the navigation service 104. Each user account record is a data structure that includes information that describes aspects of a particular user. Further details regarding an example account record stored in the database 120 are discussed below in reference to FIG. 3.

FIG. 1 also illustrates a third party application 124 executing on the third party server 108 that may offer information or services to the navigation server 110 or to users of the mobile device 106. For example, the third party application 124 may be associated with any organization that conducts transactions with or provide services to users of the mobile device 106 such as a network-based marketplace. In some embodiments, the incentives provided to vehicle occupants may be redeemed or otherwise used with the third party application 124.

Figure 2:
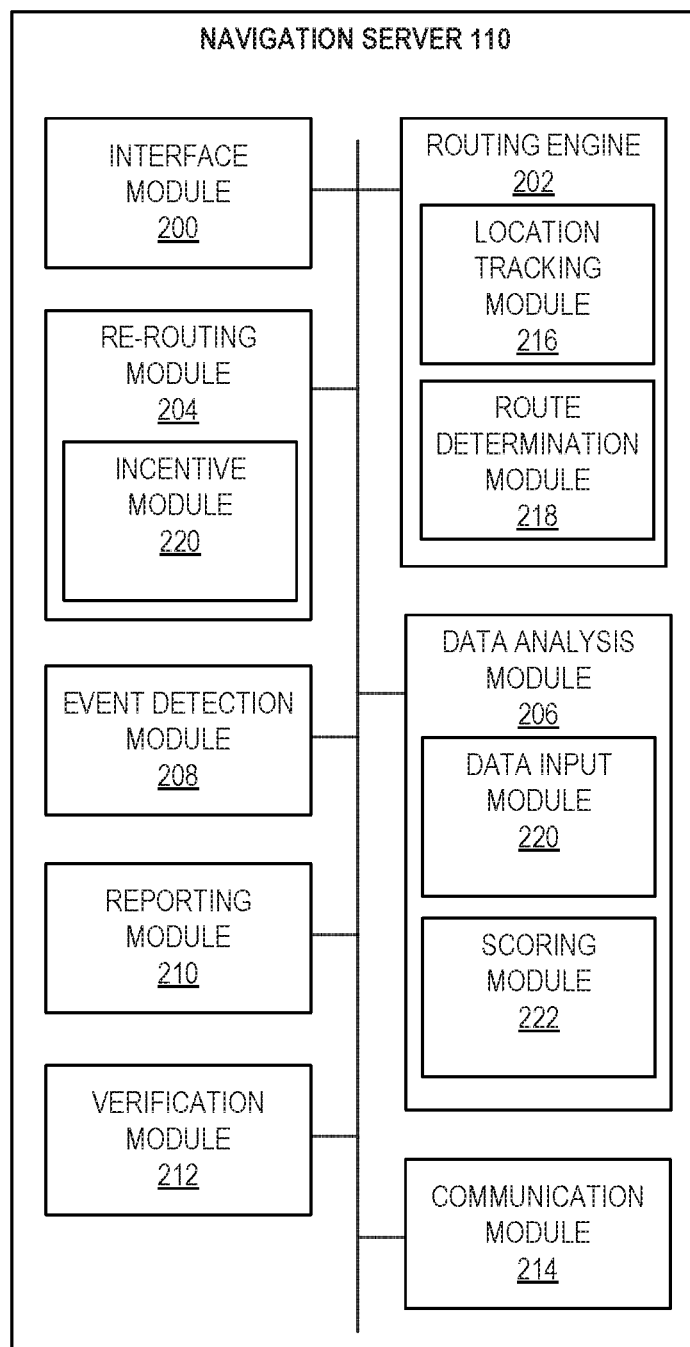
FIG. 2 is a block diagram illustrating various functional components of a navigation server, which is provided as part of the navigation system, according to example embodiments.

FIG. 2 is a block diagram depicting various functional components of the navigation server 110, which is provided as part of the navigation system 100, according to example embodiments. The mobile device 106 may be similarly configured to include at least a portion of the functional components of the navigation server 110, consistent with some embodiments. As is understood by skilled artisans in the relevant computer and Internet-related arts, each component (e.g., a module or engine) illustrated in FIG. 2 may be implemented using hardware (e.g., a processor of a machine) or a combination of logic (e.g., executable software instructions) and hardware (e.g., memory and processor of a machine) for executing the logic. Further, each component illustrated in FIG. 2 may be hosted on dedicated or shared server machines that are communicatively coupled to enable communications between server machines.

The navigation server 110 is illustrated in FIG. 2 as including an interface module 200, a routing engine 202, a re-routing module 204, a data analysis module 206, an event detection module 208, a reporting module 210, a verification module 212, and a communication module 214, all configured to communicate with each other (e.g., via a bus, shared memory, a switch, or application programming interfaces (APIs)). Each of the various components of the navigation application 112 may access one or more network databases (e.g., database 120), and each of the various components of the navigation application 112 may be in communication with one or more of the third party applications. Further, while the components depicted in FIG. 2 are discussed in the singular sense, it will be appreciated that in other embodiments multiple instances of any one of these components may be employed.

The interface module 200 is responsible for generating and displaying various GUIs for presenting information related to the navigation functionalities discussed herein. For example, the interface module 200 may provide a GUI that allows users to input an identifier of a destination location and select from among multiple routes to the destination location. The interface module 200 may also provide a GUI that includes a map display that includes a display of a current route to a destination location. The interface module 200 may update such interfaces to display alternative destinations, alternative routes, and messages related thereto. The interface module 200 is further to provide presentation data to the mobile device 106 to cause the mobile device 106 to display the GUI. The presentation data include content for rendering on a display of the mobile device 106 as well as instructions to cause the mobile device 106 to render the content. The presentation data may be stored permanently or temporarily by the mobile device 106 to enable rendering. In some embodiments, the interface module 200 functions as an API to receive client requests from an application executing on the mobile device 106 or from the third party application 124 executing on the third party server 108.

The routing engine 202 is responsible for providing routes to navigation-enabled devices (e.g., mobile device 106) to aid in navigating vehicles from their current location to the destination location. To this end, the routing engine 202 includes a location tracking module 216 for monitoring locations of navigation-enabled devices, and a route determination module 218 for selecting routes. The location tracking module 216 determine a location of a navigation-enabled device by obtaining location information (e.g., GPS data) from a location component (e.g., a GPS component) of the navigation-enabled device. The location tracking module 216 logs determined locations in a location history field of a user account record associated with the navigation-enabled device (e.g., corresponding to a user of the navigation-enabled device).

The route determination module 218 uses the determined location of the navigation-enabled device along with a destination location identifier (e.g., an address) to determine possible routes from the current location of the navigation-enabled device to the destination location. The destination location identifier may be received as user input entered via an interface provided by the interface module 200 or may be obtained from a location history field of an associated user account record. Upon determining the possible routes, the route determination module 218 determines a travel time associated with each possible route based on route distance and, in some embodiments, traffic information. The route determination module 218 ranks possible routes by associated travel time and selects the route with the shortest associated travel time as a primary route to the destination location. The routing engine 202 may work in conjunction with the interface module 200 to provide a display of the primary route in a map display presented on the navigation-enabled device.

The re-routing module 204 is responsible for re-routing vehicles to control traffic flow. To this end, the re-routing module 204 generates and provides detour suggestions to navigation-enabled devices embedded in vehicles or carried by vehicle occupants. In some instances, the re-routing module 204 may proactively provide detour suggestions to users who have opted into participation in re-routing services. In some instances, the re-routing module 204 provides detour suggestions to navigation-enabled devices based on frustration levels of vehicle occupants determined based on input component data obtained from input components (e.g., sensors) embedded in or coupled to navigation-enabled devices. The detour suggestions provided by the re-routing module 204 may include an alternative route to the destination location or a route to an alternative destination.

The re-routing module 204 may select alternative routes that are different than the primary route of the vehicle as determined by the routing engine 202, which, in some instances, may be the current route of the vehicle. In this way, the re-routing module 204 seeks to route vehicles along routes other than the routes with the shortest determined travel times, which are typically the routes most frequented by vehicles. In some instances, participating users may specify a travel time criteria that may include an allowable difference in travel times between primary routes and alternative routes. In these instances, the re-routing module 204 selects alternative routes by determining delta values corresponding to a travel time difference between the primary route and possible other routes, and selecting an alternative route from the possible other routes that has an associated delta value in accordance with the travel time criteria specified in a user preferences field of a user account record of the vehicle occupant.

The re-routing module 204 may select alternative destinations based on information included in a user account record of a vehicle occupant. For example, the re-routing module 204 may select an alternative location from among multiple locations that are within a user defined distance of the current location or current route of the vehicle. As another example, the re-routing module 204 selects an alternative location from a location history included in the user account record of the vehicle occupant (e.g., a location other than the destination location that the user travels to frequently). In another example, the re-routing module 204 selects an alternative location from a transaction history included in the user account record of the vehicle occupant (e.g., a location from which the vehicle occupant has purchased one or more items). In some instances, the alternative location may be a brick-and-mortar retail location.

Detour suggestions provided by the re-routing module 204 may further include one or more incentives (e.g., monetary incentives) to encourage vehicle occupants to accept detour suggestions and route their vehicles accordingly. As an example, users of the navigation system 100 may be provided an option to participate in re-routing services provided by the re-routing module 204. In some embodiments, users who opt-in to participation may be requested to contribute a tributary amount of value (e.g., in currency or reward points) toward a participation pool. In facilitating user contributions to the participation pool, the re-routing module 204 reduces a value included in an account balance field of a user account record of the contributing user by the tributary amount. Consistent with these embodiments, upon detecting a participating user's vehicle traveling along an alternative route, the re-routing module 204 transfers a participatory amount of value (e.g., currency or rewards points) to the participating user's account. More specifically, in transferring the participatory amount to the participating user's account, the re-routing module 204 reduces the aggregated amount of value in the participation pool by a participatory amount, and increases a value in an entry of an account balance field of a user account record corresponding to the participating user by the participatory amount.

In other embodiments, upon detecting a participating user's vehicle traveling along an alternative route, the re-routing module 204 transfers a participatory amount of value (e.g., currency or rewards points) to the participating user's account (e.g., by increasing a value in an entry of the account balance field of the corresponding user account record), and transfers a tributary amount of value out of user accounts corresponding to users whose vehicles continue to travel along primary routes (e.g., by decreasing a value in an entry of the account balance field of the corresponding user account record).

The participatory amount may be a fixed amount for all participating users of the navigation system 100 or a variable amount determined by an incentive module 220 based on a length of the alternative route, a travel time associated with the alternative route, a travel time difference between the alternative route and primary route, a number of vehicles traveling along the primary route that have occupants that are users of the navigation system 100, or a frustration level of a vehicle occupant. The tributary amount may be a fixed amount for all participating users of the navigation system 100 or a variable amount determined by the incentive module 220 based on a number of vehicles traveling along the primary route that have occupants that are users of the navigation system 100. For example, the incentive module 220 may determine the tributary amount by dividing the participatory amount by the number of vehicles traveling along the primary route that have occupants that are users of the navigation system 100.

In instances in which the detour suggestions provided by the re-routing module 204 include an alternative location, the detour suggestions may include a monetary incentive (e.g., a monetary reward or coupon) obtained by the incentive module 220. The incentive module 220 may obtain a monetary incentive from a table stored in database 120 or from a third party computing system (e.g., third party server 108) corresponding to the alternative location. The obtaining of the monetary incentive may include determining a value of the monetary incentive. The incentive module 220 may determine the value of the monetary incentive based on, for example, a frustration level of a vehicle occupant, a distance of the alternative location from the current location of the vehicle, or a distance of the alternative location from the current route of the vehicle.

The data analysis module 206 is responsible for determining frustration levels of vehicle occupants. More specifically, the data analysis module 206 is responsible for determining frustration scores associated with navigation-enabled devices included in traveling vehicles (e.g., embedded in the vehicle or carried by a vehicle occupant) using input component data received from one or more input components embedded in or coupled to navigation-enabled devices. Upon determining the frustration score associated with the navigation-enabled device, the data analysis module 206 stores a record of the frustration score in a field of the user account record of the user of the navigation-enabled device who is also the vehicle occupant.

Individual frustration scores determined by the data analysis module 206 provide a measure of frustration (e.g., a feeling of being upset or annoyed) of the user of the navigation-enabled device. Because the user of the navigation-enabled device is an occupant of the vehicle in which the navigation-enabled device resides, the frustration score is likely to provide a measure of the frustration level of the user as it relates to being in traffic. In this way, the frustration score may, in some instances, be used as a proxy for the amount of traffic in the area surrounding the user. Hence, the frustration scores determined by the data analysis module 206 may, in some embodiments, be used to automatically trigger the re-routing module 204 to provide a detour suggestion to the corresponding navigation-enabled mobile device in order to control traffic.

As shown, the data analysis module 206 includes a data input module 220 and a scoring module 222. The data input module 220 obtains input component data (e.g., raw sensor data) from one or more input components embedded in or coupled to the navigation-enabled devices. The one or more input components may, for example, include microphones, motion sensors (e.g., accelerometers, gravity sensors, gyroscopes, and rotational vector sensors), and heart rate sensors. Accordingly, the input component data may, for example, include audio data, motion data, and heart rate data. The input components may be embedded in the navigation-enabled device, embedded in a wearable device worn by an occupant of the vehicle and coupled to the navigation-enabled device, or embedded in the vehicle and coupled to the navigation-enabled device.

The scoring module 222 scores the input component data (e.g., raw input component data) obtained by the data input module 220, and aggregates the input component data scores to determine the frustration score associated with the navigation-enabled device. The manner in which the scoring module 222 scores input component data depends on the type of input component data being scored. For example, scoring audio data includes determining an audio level of the audio data and scoring the audio data based on a value of the audio level. The scoring module 222 may further score the audio data by using a speech recognition algorithm to identify key words from the audio data and comparing the identified keywords to a repository of keywords stored in the database 120. The repository of keywords may, for example, include language that is known to be commonly used when an occupant of a vehicle is frustrated, specifically frustrated while in traffic. The scoring of the audio data may further include determining a number of identified keywords from the audio data that are present in the repository of keywords stored in the network accessible database and scoring the audio data based thereon.

As another example of scoring input component data, the scoring of motion data includes determining a velocity or frequency of motion of the navigation-enabled device from the motion data and scoring the motion data based on the velocity and/or frequency of motion. In this example, the motion of the navigation-enabled device may be due to a vehicle occupant making a hand gesture or otherwise using their hands to express frustration while holding the navigation-enabled device (e.g., pounding a vehicle steering wheel with navigation-enabled device in hand). As yet another example, the scoring of heart rate data includes determining a heart rate of the user based on heart rate data received from the heart rate sensor.

In some embodiments, the scoring module 222 scores the input component data based on a comparison of the input component data with baseline data included in a user account record of an occupant of the vehicle. The baseline data includes previous input component data captured while the user is in a relaxed and non-frustrated state. Upon registering as a user with the navigation system 100, users may be instructed to capture baseline data in such a manner. Consistent with these embodiments, the scoring module 222 scores the input component data by performing operations including comparing values of input component data with values in baseline data, and calculating a delta value (e.g., a difference in values) between the input component data and the baseline data. Further details regarding the scoring of input component data based on a comparison with baseline data are discussed below in reference to FIG. 7, according to some embodiments.

The scoring module 222 aggregates the input component data scores to determine the overall frustration score associated with the navigation-enabled device. As an example, in some embodiments, the scoring module 222 may sum each individual input component data score to compute the overall frustration score. Because the navigation-enabled device is either carried by the vehicle occupant or included in the vehicle, the frustration score provides a measure of the frustration level of the vehicle occupant.

The event detection module 208 detects traffic disruption events based on frustration levels of vehicle occupants. More specifically, the event detection module 208 detects traffic disruption events based on frustration scores determined by the data analysis module 206 from sensors embedded in or coupled to navigation-enabled devices embedded in vehicles or carried by vehicle occupants. The traffic disruption event may include or be caused by a variety of different event types including, for example, accidents, construction road closures, police and speed traps, or a road hazard.

The event detection module 208 detects traffic disruption events by determining that a threshold number of a group of navigation-enabled devices have an associated frustration score (e.g., a frustration score determined from input components embedded in or coupled to the device) that is above a threshold score. The threshold score may be set by an administrator or user of the navigation system 100, or learned from a history of frustration scores associated with the device. The threshold number of devices may depend on the number of devices in the group. For example, the threshold number may include a certain percentage of the group (e.g., 50%). The group of navigation-enabled devices may be devices within a predefined distance of one another or devices within a predefined distance of a particular location. The predefined distance may be a fixed distance set by an administrator of the navigation system 100 or may be a variable distance based on a traffic flow rate in the area.

The reporting module 210 generates, in an automated manner without user intervention, traffic disruption report data in response to the event detection module 208 detecting traffic disruption events. The traffic disruption report data includes a record of the traffic disruption event, an identifier of the location of the traffic disruption event (e.g., an address or GPS coordinates), and a time stamp corresponding to when the traffic disruption event was detected. The reporting module 210 stores the traffic disruption report data in the database 120 for subsequent access and retrieval.

The verification module 212 verifies existing traffic report data. The existing traffic report data may be maintained in the database 120 or retrieved from a third-party navigation system hosted by the third party server 108. The existing traffic report data may be based on user generated traffic disruption reports.

In verifying existing traffic report data, the verification module 212 determines whether a traffic disruption event has been detected at a location of the existing traffic report data based on frustration levels of nearby vehicle occupants determined by the data analysis module 206. If the verification module 212 determines that a traffic disruption event has been detected, the verification module 212 issues a verification of the existing traffic report data, and the existing traffic report data is maintained. If the verification module 212 determines that a traffic disruption event has not been detected, the verification module 212 issues a rejection of the existing traffic disruption report data and as such, the existing traffic disruption report data may be deleted. In instances in which the existing traffic disruption data is maintained by the navigation system 100, the navigation system 100 may automatically remove the existing traffic disruption data from the database 120.

The communication module 214 is responsible for publishing messages to navigation-enabled devices among other devices. In doing so, the communication module 214 may utilize any one of a number of message delivery networks and platforms to deliver messages such as, for example, electronic mail (email), push notifications, instant message (WI), Short Message Service (SMS), text, facsimile, or voice (e.g., Voice over IP (VoIP)) messages. For example, the communication module 214 publishes messages to navigation-enabled devices to notify users of a nearby traffic disruption event. As another example, the communication module 214 publishes messages to navigation-enabled devices that include detour suggestions generated by the re-routing module 204.

Figure 3:
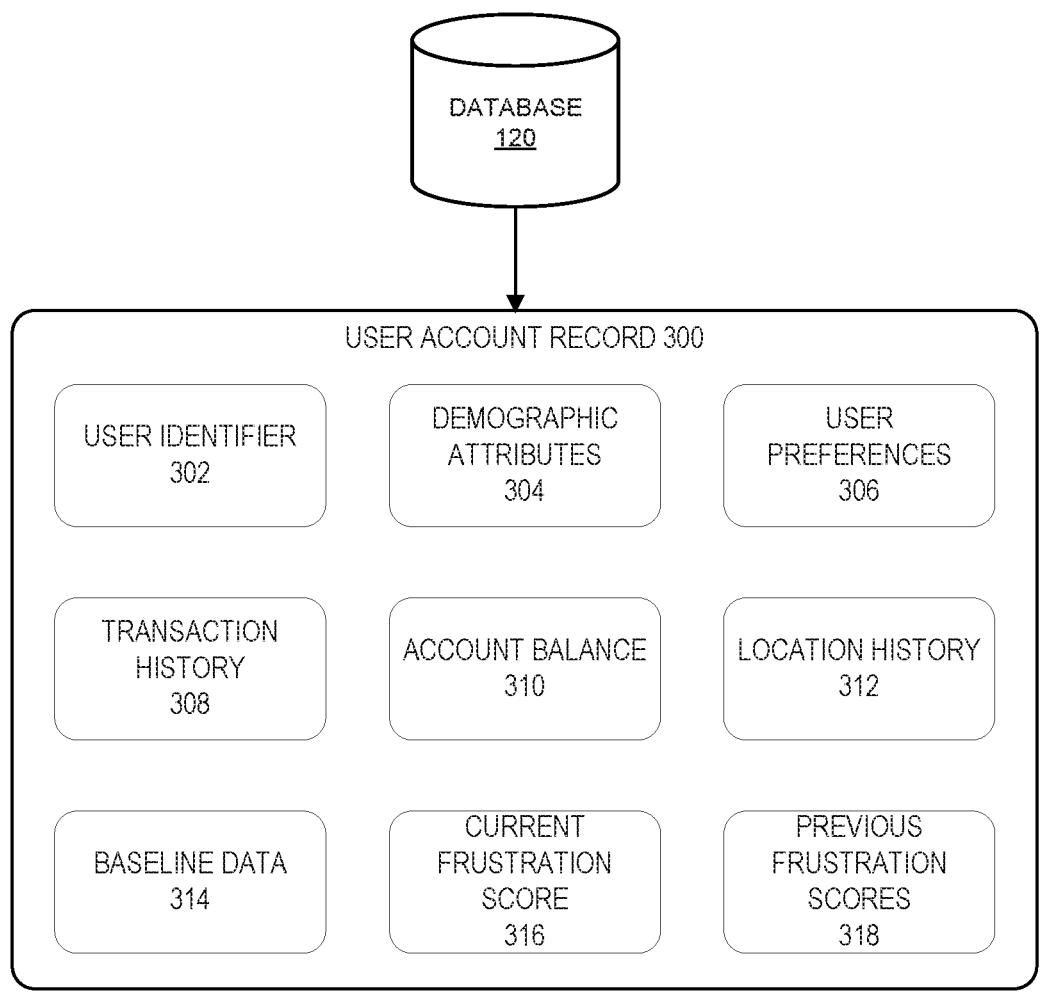
FIG. 3 is a data architecture diagram illustrating an example user account record, which is a data structure stored in a database of the navigation system, according to example embodiments.

FIG. 3 is a data architecture diagram illustrating an example user account record 300, which is a data structure stored in the database 120 of the navigation system 100, according to example embodiments. As shown, the user account record 300 contains multiple fields including user identifier 302, demographic attributes 304, user preferences 306, transaction history 308, account balance 310, location history 312, baseline data 314, current frustration score 316, and previous frustration scores 318. The user identifier 302 field includes an identifier (e.g., an account number, a name, or a profile name) of the user to which the user account record 300 corresponds.

Entries within the demographic attributes 304 field include one or more demographic attributes that describe aspects of the user. The demographic attributes may, for example, include gender, age, location, employment status, education history, or the like.

Entries within the user preferences 306 field include user preferences associated with the functions of the navigation system 100. User preferences may be actively obtained from information requested from and provided by the user, or passively obtained by monitoring interactions of the user with the navigation system 100 (e.g., monitoring locations visited by the user and routes used to travel to locations). User preferences may, for example, relate to preferred destinations (e.g., previously visited destinations), preferred routes to destinations (e.g., routes previously used to travel to particular locations), preference for participation in re-routing services (e.g., whether the user has opted-in to participation in re-routing services), preferred times for re-routing (e.g., during the weekday, but not during the weekend), and allowable travel time differences for re-routing (e.g., a travel time difference between a current or primary route and an alternative route).

The transaction history 308 field includes entries related to a history of items purchased by the user. The transaction history 308 may, for example, be obtained from a third party server (e.g., the third party server 108) hosting an online marketplace.

The account balance 310 field includes an entry corresponding to an amount of accumulated value (e.g., in a commercial currency, such as the U.S. dollar or a proprietary currency, such as "points"). The accumulated value may, for example, be transferred to another account of the user (e.g., a bank account), transferred to another user's account, redeemed for products or services, or used to purchase products or services.

The location history 312 field includes entries corresponding to previous locations visited by the user as determined by the location tracking module 216. Entries within the location history 312 field include identifiers of the previous locations such as geographical coordinates or addresses.

The baseline data 314 includes values for input component data obtained from input components embedded in or coupled to a navigation-enabled device of the user (e.g., the mobile device 106). More specifically, the baseline data 314 includes input component data captured while the user is in a relaxed state, which may be used as a point of reference to aid in the determination of the frustration level of the user.

The current frustration score 316 field includes an entry corresponding to the most recent frustration score of the user determined by the scoring module 222. The previous frustration scores 318, on the other hand, include entries corresponding to previous frustration scores of the user determined by the scoring module 222.

Figure 4:
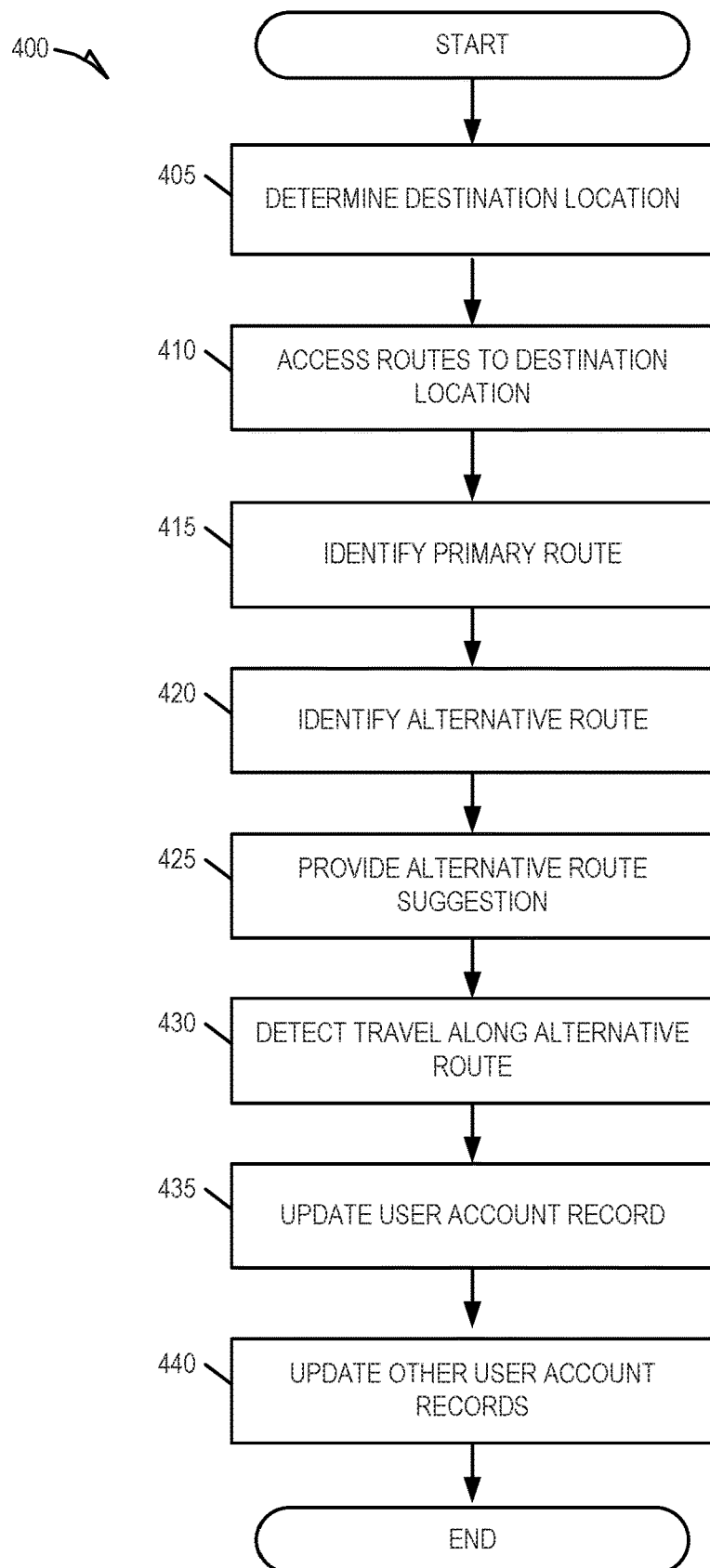
FIG. 4 is a flow chart illustrating a method for proactive rerouting of a vehicle traveling to a destination location using incentives, according to an example embodiment.

FIG. 4 is a flow chart illustrating a method 400 for proactive rerouting of a vehicle traveling to a destination location using incentives, according to an example embodiment. The method 400 may be embodied in computer-readable instructions for execution by one or more processors such that the steps of the method 400 may be performed in part or in whole by functional components (e.g., modules) of the mobile device 106 or the navigation server 110; accordingly, the method 400 is described below by way of example with reference thereto. However, it shall be appreciated that the method 400 may be deployed on various other hardware configurations and is not intended to be limited to the functional components of the mobile device 106 or the navigation server 110.

At operation 405, the routing engine 202 determines a destination location of a vehicle. The routing engine 202 determines the destination location of the vehicle from information received from a navigation-enabled device (e.g., mobile device 106), which may be embedded in the vehicle or carried by an occupant of the vehicle. For example, in some instances, the routing engine 202 determines the destination location of the vehicle based on input received, via an interface presented on the navigation-enabled device provided by the interface module 200, from the user such as an identifier (e.g., an address) of the destination location. In other instances, the routing engine 202 determines the destination location of the vehicle using calendar data (e.g., obtained from the navigation-enabled device) that includes a location of a calendar event.

In still other instances, the routing engine 202 determines the destination location using a combination of current location information (e.g., GPS data) obtained from a location component (e.g., a GPS component) of the navigation-enabled device and location history associated with the vehicle. As an example, the routing engine 202 may determine the destination location using a location history included in a user account record of a vehicle occupant. In this example, the routing engine 202 determines the destination location based on the location information indicating the vehicle occupant, and thus the vehicle, is traveling in the direction of a location previously visited by the vehicle occupant as indicated in the location history of the vehicle occupant.

At operation 410, the routing engine 202 identifies possible routes to the destination location originating from a current location of the navigation-enabled device. The routing engine 202 may determine a current location of the navigation-enabled device from user input received via an interface presented on the navigation-enabled device or by querying a location component (e.g. a GPS transceiver) embedded in the navigation-enabled device. In identifying the possible routes to the destination location, the routing engine 202 may access map data including the current location and destination location to identify each possible path between each location, or the routing engine 202 may access previously determined routes stored in the database 120 or provided by a third party service (e.g., operating on the third party server).

At operation 415, the routing engine 202 identifies a primary route from among the possible routes to the destination location. The primary route is selected by the routing engine 202 from among the possible routes to the destination location based on a travel time to the destination location when using the primary route. More specifically, the routing engine 202 may identify the primary route by determining a travel time associated with each possible route, ranking each route according to determined travel time, and selecting the route with the shortest associated travel time as the primary route. The travel time may be determined based on a combination of the distance traveled in the route and current traffic conditions.

At operation 420, which is optional in some embodiments, the re-routing module 204 selects an alternative route to the destination location. The alternative route is a route other than the primary route. In some embodiments, the alternative route is identified by the re-routing based on user preferences included in a user account record of an occupant of the vehicle. For example, the user preferences may include a constraint on an amount of additional travel time for re-routing to an alternative route. In these embodiments, the selecting of the alternative route includes determining a delta value between travel times associated with the primary route and the other possible routes, where the delta value is determined by taking the difference in travel times between the primary route and another route. The selecting of the alternative route further includes determining that the delta value is in accordance with the travel time constraint included in the user preference field of the user account data record of the vehicle occupant.

At operation 425, which is also optional in some embodiments, the interface module 200 provides the alternative route suggestion by causing display of a user interface on the navigation-enabled device that includes a message including the alternative route along with an incentive for the occupant of the vehicle to direct the vehicle to the alternative route. The incentive may, for example, include an amount of value corresponding to currency or rewards points. The amount of value may, in some instances, be a fixed amount for all users of the navigation system 100, and in other instances, may be a variable amount determined, for example, based on a number of vehicles traveling along the primary route, a travel time associated with the alternative route, or a delta value corresponding to the difference in travel time between the alternative route and the primary route.

At operation 430, the location tracking module 216 detects the vehicle traveling along the alternative route. The location tracking module 216 detects the vehicle traveling along the alternative route based on location information (e.g., GPS data) received from a location component (e.g., GPS component) of the navigation-enabled device. More specifically, the location tracking module 216 compares location information obtained from the navigation-enabled device with location information (e.g., GPS coordinates) associated with the alternative route to determine that the vehicle is traveling along the alternative route. In some embodiments, the operation 430 may occur without operations 420 and 425, and in this manner, the location tracking module 216 detects the vehicle traveling along a route other than the primary route consistent with the methodologies referenced above.

At operation 435, the incentive module 220 updates a user account record (e.g., user account record 300) corresponding to an occupant of the vehicle in response to detecting the vehicle traveling along the alternative route. More specifically, the incentive module 220 updates an entry in the user account record by increasing a value in the account balance field by a participatory quantity. In some embodiments, the participatory quantity is a fixed amount for all users of the navigation system 100. In some embodiments, the participatory quantity is a variable amount based on a number of vehicles traveling along the primary route, a travel time associated with the alternative route, a delta value corresponding to the difference in travel time between the alternative route and the primary route, or various combinations thereof.

At operation 440, the incentive module 220 updates, in response to detecting the vehicle traveling along the alternative route, other user account records corresponding to occupants of other vehicles traveling along the primary route. In updating the other user account records, the incentive module 220 updates an entry in the user account records corresponding to an account balance field. In particular, the incentive module 220 decreases a current value of the entry in the account balance field by a tributary quantity. In some embodiments, the tributary quantity is a fixed amount for all users of the navigation system 100. In some embodiments, the tributary quantity is based on a number vehicles traveling along the primary route. For example, the incentive module 220 may determine the tributary quantity by dividing the participatory quantity by the number of vehicles traveling along the primary route.

Figure 5:
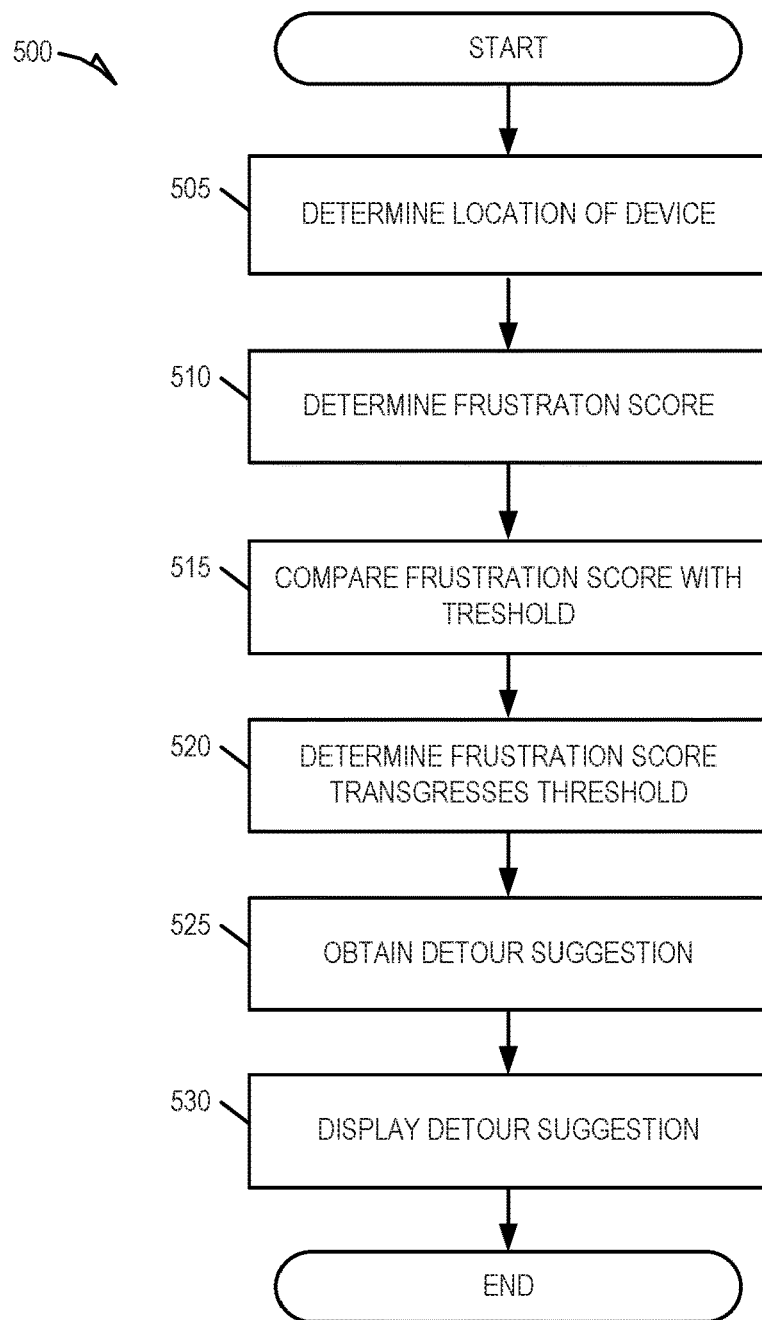
FIG. 5 is a flow chart illustrating a method for proactive rerouting of a traveling vehicle based on a frustration level of a vehicle occupant, according to an example embodiment.

FIG. 5 is a flow chart illustrating a method 500 for proactive rerouting of a traveling vehicle based on a frustration level of a vehicle occupant, according to an example embodiment. The method 500 may be embodied in computer-readable instructions for execution by one or more processors such that the steps of the method 500 may be performed in part or in whole by functional components (e.g., modules) of the mobile device 106 or the navigation server 110; accordingly, the method 500 is described below by way of example with reference thereto. However, it shall be appreciated that the method 500 may be deployed on various other hardware configurations and is not intended to be limited to the functional components of the mobile device 106 or the navigation server 110.

At operation 505, the location tracking module 216 determines a location of a vehicle based on location information (e.g., GPS data) received from a location component (e.g., GPS data) of a navigation-enabled device embedded in the vehicle or carried by an occupant (e.g., driver or passenger) of the vehicle.

At operation 510, the data analysis module 206 determines a frustration score associated with the navigation-enabled device based on input component data obtained from input components coupled to or embedded in the navigation-enabled device. Because the navigation-enabled device is embedded in the vehicle or carried by an occupant of the vehicle, the frustration score may also be considered to be associated with the vehicle. The frustration score provides a measure of frustration of a user of the navigation-enabled device who is an occupant of the vehicle. Further details regarding the determination of the frustration score are discussed below in reference to FIG. 6, according to some example embodiments.

At operation 515, the data analysis module 206 compares the frustration score associated with the navigation-enabled device with a threshold frustration score. In some embodiments, the threshold frustration score may be set by the user or an administrator of the navigation system 100. In some embodiments, the frustration score threshold is based on previous frustration scores of the vehicle occupant.

At operation 520, the data analysis module 206 determines that the frustration score associated with the navigation-enabled device transgresses the frustration score threshold. For example, the data analysis module 206 determines that the frustration score is above the frustration score threshold. The determination that the frustration score associated with the navigation-enabled device is above the frustration score threshold provides an indication that the frustration level of the vehicle occupant has risen to a level in which re-routing the vehicle may be beneficial.

In response to determining that the frustration score transgresses the frustration score threshold, the re-routing module 204 at operation 525 obtains a detour suggestion for the vehicle. The detour suggestion may include an alternative route to a destination location of the vehicle or a route to an alternative destination. In either event, the detour suggestion is provided to remove the vehicle from its current route with the intent of reducing the frustration score associated with the navigation-enabled device, which is in effect reducing the frustration level of the occupant of the vehicle.

In instances in which the detour suggestion includes an alternative destination, the detour suggestion may further include a monetary incentive for the vehicle occupant to direct the vehicle to travel to the alternative location. For example, the detour suggestion may include a coupon, rebate, or discount to a brick-and-mortar retail location corresponding to the alternative destination. In instances in which the detour suggestion includes an incentive for the vehicle occupant to direct the vehicle to the alternative destination, the obtaining of the detour destination by the re-routing module 204 includes working in conjunction with the incentive module 220 to determine a value of the monetary incentive. As an example, the incentive module 220 may determine the value of the monetary incentive based on the frustration score associated with the navigation-enabled device such that the higher the frustration score, the higher the monetary incentive will be. As another example, the incentive module 220 may determine of the value of the monetary incentive based on a distance from the current location of the vehicle to the alternative location. In some embodiments, the obtaining of the detour suggestion also includes identifying a specific brick-and-mortar retail location based on user preferences (e.g., a transaction history or location history) included in a user account record of an occupant of the vehicle.

Figure 14A:
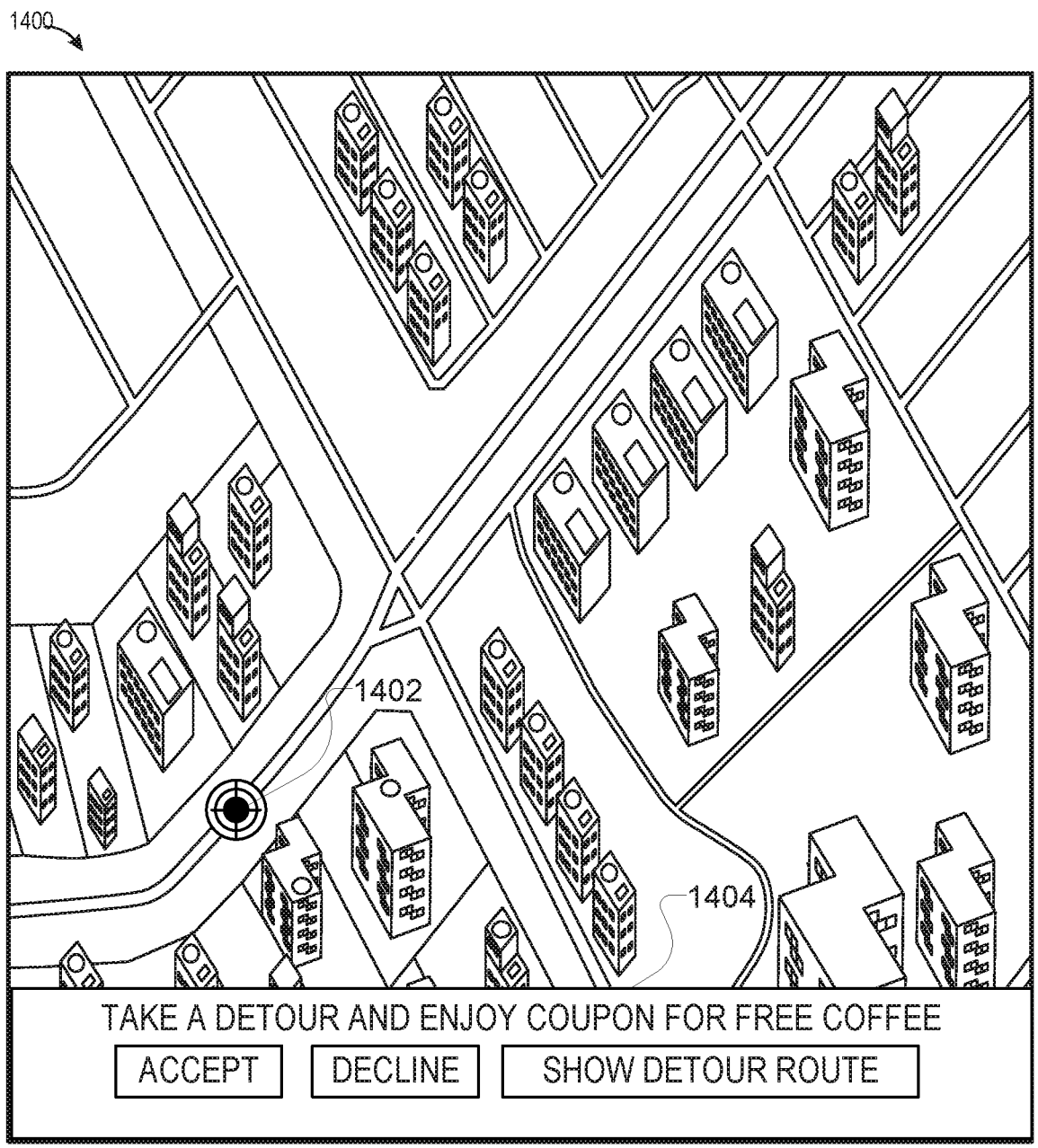
FIG. 14A is an interface diagram illustrating a user interface displaying a current location of a vehicle and a detour suggestion including an alternative destination, according to an example embodiment.
Figure 14B:
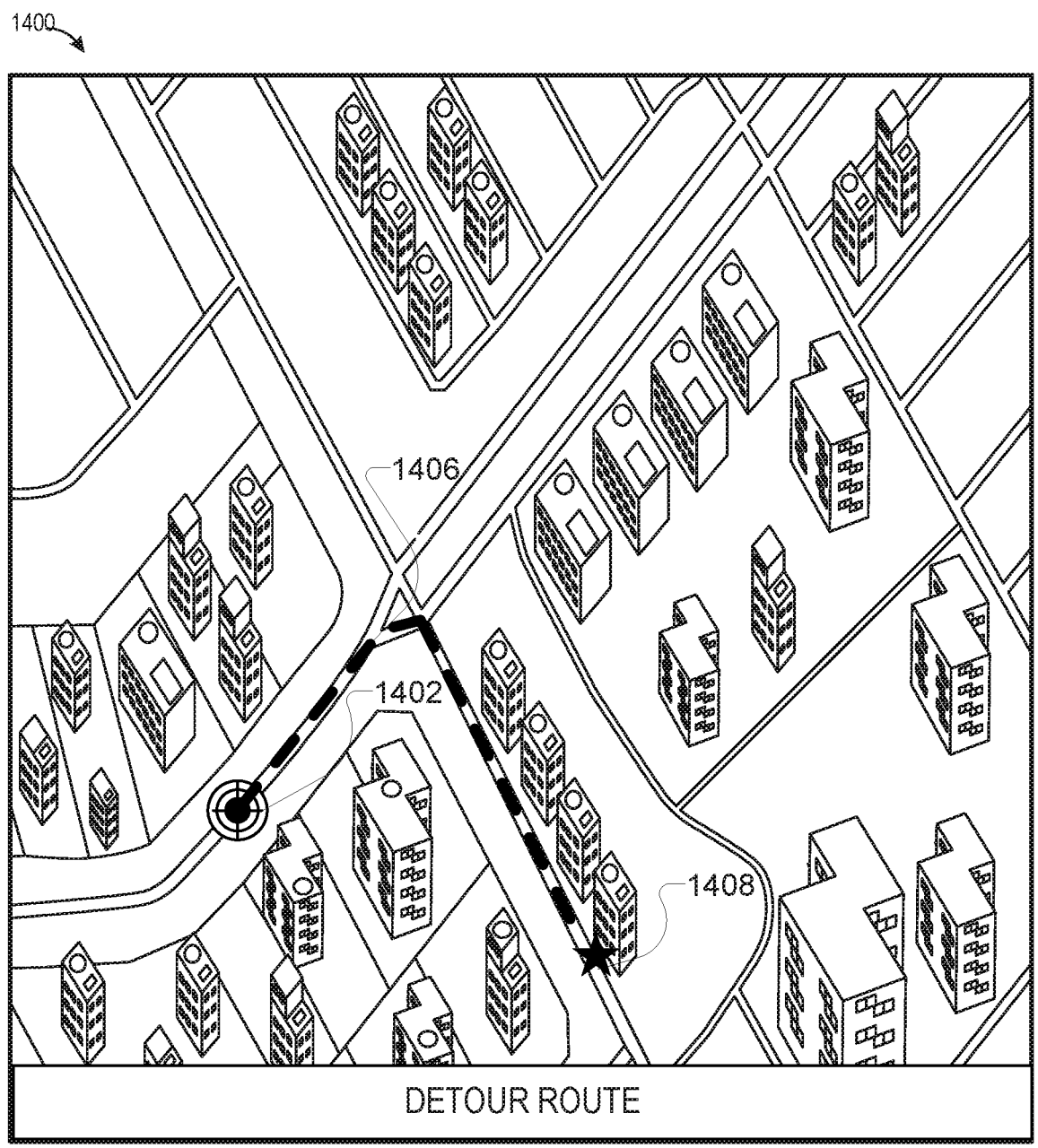
FIG. 14B is an interface diagram illustrating an updated user interface that has been modified to display a detour route to the alternative destination, according to an example embodiment.

At operation 530, the interface module 200 causes display of the detour suggestion on the navigation-enabled device. The detour suggestion may be presented within a user interface that includes a map display. The user interface may further include or may be updated to include an indication of the current location of the user, a current route of the user, and a destination location of the user along with an alternative route or an alternative destination where applicable. Further, the display of the detour suggestion may include a display of the monetary incentive for the user to visit the alternative destination. An example of displaying the detour suggestion is illustrated in FIGS. 14A and 14B, and discussed below in reference thereto, according to some example embodiments.

Figure 6:
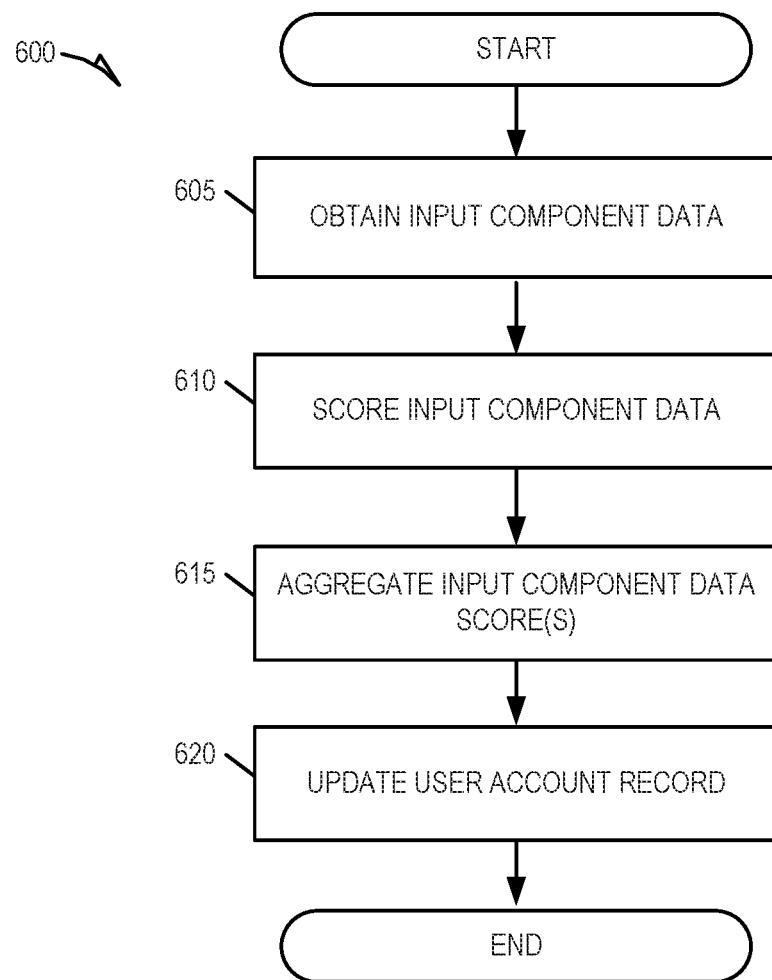
FIG. 6 is a flow chart illustrating a method for determining a frustration level of a vehicle occupant based on input component data, according to an example embodiment.

FIG. 6 is a flow chart illustrating a method 600 for determining a frustration level of a vehicle occupant based on input component data, according to an example embodiment. Consistent with some embodiments, the operations of method 600 are performed as part of operation 510 of method 500. The method 600 may be embodied in computer-readable instructions for execution by one or more processors such that the steps of the method 600 may be performed in part or in whole by functional components (e.g., modules) of a mobile device 106 or the navigation server 110; accordingly, the method 600 is described below by way of example with reference thereto. However, it shall be appreciated that the method 600 may be deployed on various other hardware configurations and is not intended to be limited to the functional components of the mobile device 106 or the navigation server 110.

At operation 605, the data input module 220 obtains input component data from one or more input components embedded in or coupled to a navigation-enabled device (e.g., mobile device 106) carried by an occupant of the vehicle or included in the vehicle. The one or more input components may, for example, include a microphone, a motion sensor, or a heart rate sensor. The input component data obtained from the one or more input components corresponds to the output of the input components. The input components may be embedded in the navigation-enabled device, embedded in a wearable device worn by an occupant of the vehicle and coupled to the navigation-enabled device, or embedded in the vehicle and coupled to the navigation-enabled device.

At operation 610, the scoring module 222 scores the input component data received from each of the one or more input components. The manner in which the scoring module 222 scores input component data depends on the type of input component data being scored. For example, in some instances, the scoring module 222 scores the input component data based on the absolute value thereof. As an example, in instances in which the input component data includes audio data received from a microphone embedded in or coupled to the navigation-enabled device, the determining of the frustration score includes determining an audio level of the audio data and scoring the audio data based on the value of the audio level. The scoring module 222 may further score the audio data by using a speech recognition algorithm to identify key words from the audio data and comparing the identified keywords to a repository of keywords stored in a network accessible database. The repository of keywords may, for example, include language that is known to be commonly used when an occupant of a vehicle is frustrated, specifically frustrated while sitting in traffic. The scoring of the audio data may further include determining a number of identified keywords from the audio data that are present in the repository of keywords stored in the network accessible database, and scoring the audio data based thereon.

As another example, in instances in which the input component data includes motion data from a motion sensor, the scoring of the input component data may include determining a velocity or frequency of motion of the navigation-enabled device from the motion data and scoring the motion data based on the velocity or frequency of motion. As yet another example, in instances in which the input component data includes heart rate data from a heart rate sensor, the scoring of the input component data may include determining a heart rate of the user based on heart rate data received from the heart rate sensor.

In some embodiments, the scoring module 222 scores the input component data based on a comparison of the input component data with baseline data included in a user account record of an occupant of the vehicle. Further details regarding the scoring of input component data based on a comparison with baseline data are discussed below in reference to FIG. 7, according to some embodiments.

At operation 615, the scoring module 222 aggregates the input component data scores determined at 610 to determine the overall frustration score associated with the navigation-enabled device. As an example, in some embodiments, the frustration scoring module may sum each individual input component data score to compute the overall frustration score. Because the navigation-enabled device is either carried by the vehicle occupant or included in the vehicle, the frustration score provides a measure of the frustration level of the vehicle occupant.

At operation 620, the scoring module 222 updates a user account record corresponding to an occupant of the vehicle to reflect the current frustration score of the user of the navigation-enabled device. The updating of the user account record includes adding an entry to the current frustration score field of the user account record.

Figure 7:
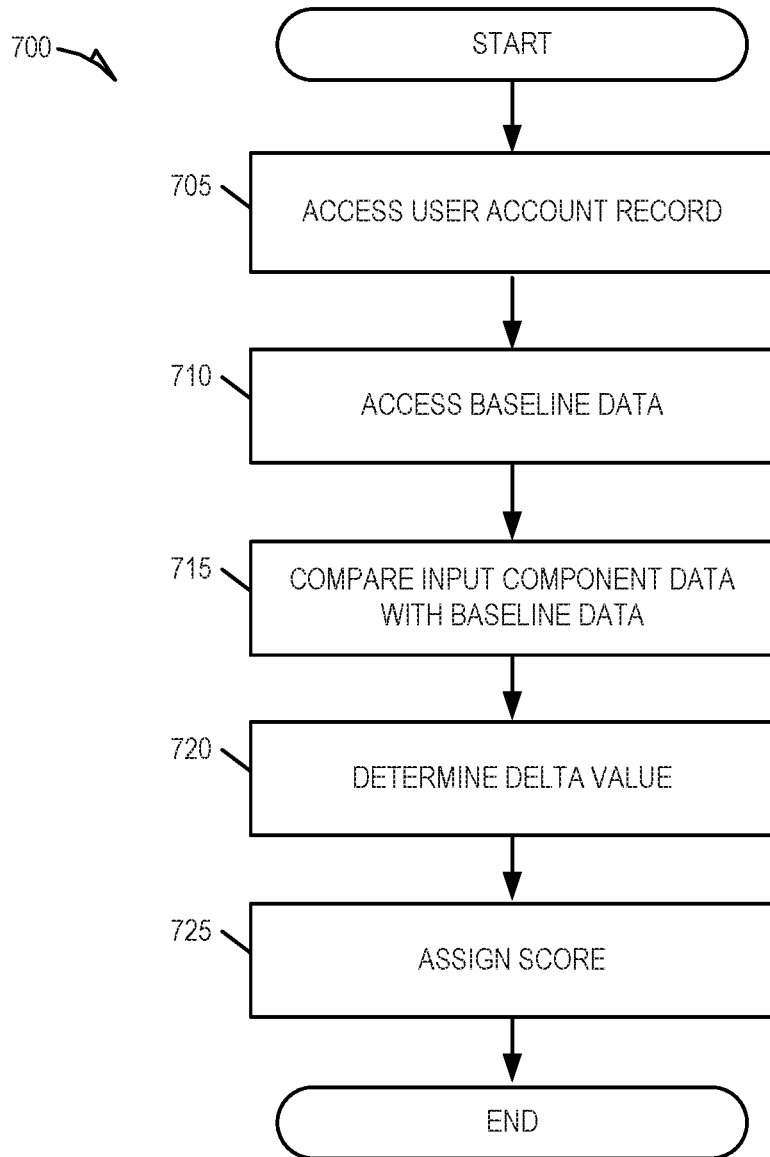
FIG. 7 is a flow chart illustrating a method for scoring input component data, according to an example embodiment.

FIG. 7 is a flow chart illustrating a method 700 for scoring input component data, according to an example embodiment. Consistent with some embodiments, the operations of method 700 are performed as part of operation 610 of the method 600. Further, the method 700 may be repeated for each type of input component data received. The method 700 may be embodied in computer-readable instructions for execution by one or more processors such that the steps of the method 700 may be performed in part or in whole by functional components (e.g., modules) of a mobile device 106 or the navigation server 110; accordingly, the method 700 is described below by way of example with reference thereto. However, it shall be appreciated that the method 600 may be deployed on various other hardware configurations and is not intended to be limited to the functional components of the mobile device 106 or the navigation server 110.

At operation 705, the scoring module 222 accesses a user account record corresponding to an occupant (e.g. a driver or passenger) of a vehicle who is also the user of the navigation-enabled device included in the vehicle. The user account record is accessed from the database 120. At operation 710, the scoring module 222 accesses baseline data included in the user account record. The baseline data includes input component data captured (e.g., from one or more input components embedded in the navigation-enabled device or another device) while the user is in a relaxed non-frustrated state. The baseline data may be captured from the user at a time when the user is establishing a user account with the navigation system 100. In this way, the baseline data serves as a point of comparison for analyzing and determining the current frustration level of the user.

At operation 715, the scoring module 222 compares the input component data received from the one or more input components embedded in or coupled to the navigation-enabled device with the baseline data included in the user account record. For example, in instances in which the input component data includes a current heart rate of the user, the comparing of the input component data with emotional baseline data includes comparing the current heart rate with a baseline heart rate of the user. As another example, in instances in which the input component data includes audio data, the comparing of the input component data with baseline data may include comparing a current audio level of the audio level (e.g., an audio level of the user's voice) with a baseline audio level (e.g., a baseline audio level of the user's voice).

At operation 720, the scoring module 222 determines a delta value between the input component data and the baseline data. The delta value corresponds to a difference in value between the input component data and the baseline data.

At operation 725, the scoring module 222 assigns a score to the input component data based on the delta value. In some embodiments, the assigning of the score to the input component data may include assigning a weight to the delta value based on the type of sensor from which the input component data has been obtained.

Figure 8:
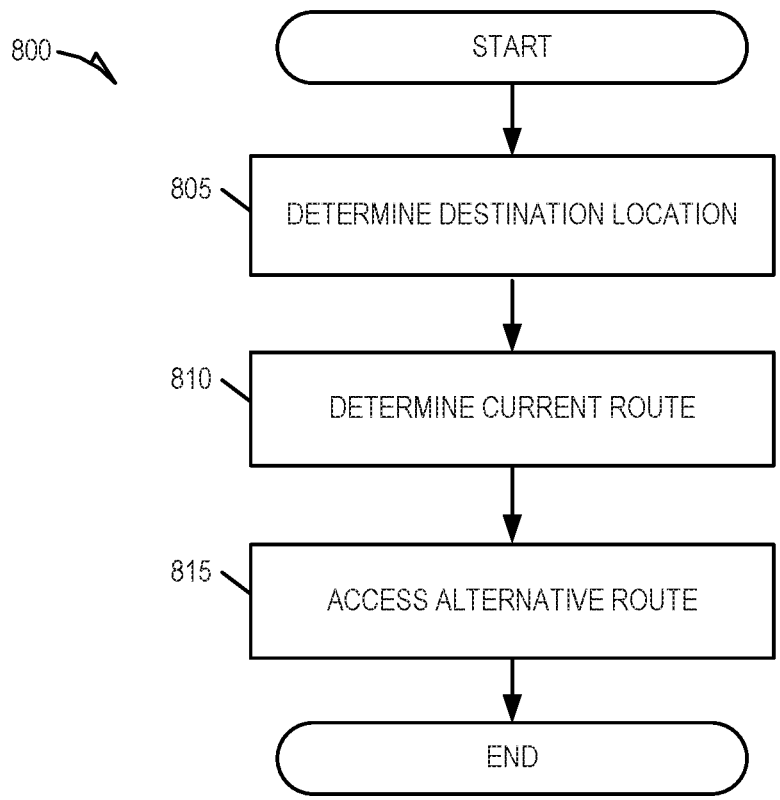
FIG. 8 is a flow chart illustrating a method of obtaining a detour suggestion for use in proactive rerouting of a traveling vehicle, according to an example embodiment.

FIG. 8 is a flow chart illustrating a method 800 of obtaining a detour suggestion for use in proactive rerouting of a traveling vehicle, according to an example embodiment. The method 800 corresponds to embodiments in which the detour suggestion includes an alternative route to a destination location. Consistent with some embodiments, the operations of the method 800 are performed as part of operation 525 of the method 500. The method 800 may be embodied in computer-readable instructions for execution by one or more processors such that the steps of the method 800 may be performed in part or in whole by functional components (e.g., modules) of a mobile device 106 or the navigation server 110; accordingly, the method 800 is described below by way of example with reference thereto. However, it shall be appreciated that the method 800 may be deployed on various other hardware configurations and is not intended to be limited to the functional components of the mobile device 106 or the navigation server 110.

At operation 805, the routing engine 202 determines a destination location of a vehicle. The routing engine 202 determines the destination location of the vehicle from information received from a navigation-enabled device (e.g., mobile device 106), which may be embedded in the vehicle or carried by an occupant of the vehicle. For example, in some instances, the routing engine 202 determines the destination location of the vehicle based on input received, via an interface presented on the navigation-enabled device provided by the interface module 200, from the user such as an identifier (e.g., an address) of the destination location. In other instances, the routing engine 202 determines the destination location of the vehicle using calendar data (e.g., obtained from the navigation-enabled device) that includes a location of a calendar event.

In still other instances, the routing engine 202 determines the destination location using a combination of current location information (e.g., GPS data) obtained from a location component (e.g., a GPS component) of the navigation-enabled device and location history associated with the vehicle. As an example, the routing engine 202 may determine the destination location using a location history included in a user account record of a vehicle occupant. In this example, the routing engine 202 determines the destination location based on the location information indicating that the vehicle occupant, and thus the vehicle, is traveling in the direction of a location previously visited by the vehicle occupant as indicated in the location history of the vehicle occupant At operation 810, the location tracking module 216 determines a current route of the vehicle. For example, the location tracking module 216 may determine the current route of the vehicle based on a route selection made by the user via an interface provided by the interface module 200 and presented on the navigation-enabled device. As another example, the location tracking module 216 may determine the current route of the vehicle based on location information (e.g. GPS data) obtained from a location component (e.g. a GPS transceiver) embedded in the navigation-enabled device.

At operation 815, the re-routing module 204 accesses an alternative route to the destination location. The re-routing application may access the alternative route based on user preference data included in a user account of the user. For example, the user preference data may include an allowable time delay between a current route and a re-routed alternative route. The alternative route is a route to the destination location other than the current route of the vehicle.

Figure 9:
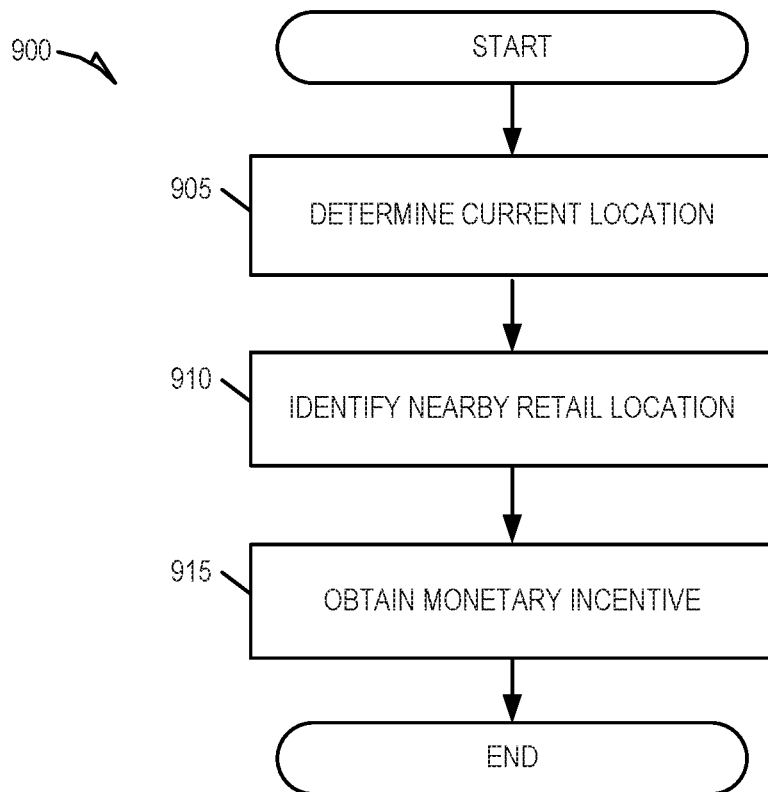
FIG. 9 is a flow chart illustrating a method of obtaining a detour suggestion for use in proactive rerouting of a traveling vehicle, according to an alternative embodiment.

FIG. 9 is a flow chart illustrating a method 900 of obtaining a detour suggestion for use in proactive rerouting of a traveling vehicle, according to an alternative embodiment. The method 900 corresponds to embodiments in which the detour suggestion includes an alternative destination. Consistent with some embodiments, the operations of method 900 are performed as part of operation 525 of the method 500. The method 900 may be embodied in computer-readable instructions for execution by one or more processors such that the steps of the method 900 may be performed in part or in whole by functional components (e.g., modules) of a mobile device 106 or the navigation server 110; accordingly, the method 900 is described below by way of example with reference thereto. However, it shall be appreciated that the method 800 may be deployed on various other hardware configurations and is not intended to be limited to the functional components of the mobile device 106 or the navigation server 110.

At operation 905, the location tracking module 216 determines a current location of a vehicle based on location information (e.g. GPS data) obtained from a location component (e.g. a GPS transceiver) embedded in a navigation-enabled device located in the vehicle.

At operation 910, the re-routing module 204 identifies a nearby retail location. More specifically, the re-routing module 204 identifies a retail location within a certain distance of the current location of the vehicle. The distance may be a user specified distance included in user preferences of a user account record corresponding to a vehicle occupant. In some embodiments, the identifying of the nearby retail location may include identifying a plurality of retail locations within a user specified distance of the current location of the vehicle, and selecting one of the retail locations based on information included in a user account record of a vehicle occupant maintained by the navigation system 100. For example, the retail location identified by the re-routing module 204 may be a user specified location included in a user preferences field included in the user account record. As another example, the retail location identified by the re-routing module 204 may be a location previously visited by the vehicle occupant included in a location history field of the user account record of the user.

At operation 915, the incentive module 220 obtains a monetary incentive for the retail location. The incentive module 220 may obtain the monetary incentive directly from a third party server corresponding to the retail location or as part of a cooperative agreement between the retail location and the navigation system 100. The obtaining of the monetary incentive includes, in some instances, determining a value of the monetary incentive. The incentive module 220 may determine the value of the monetary incentive, for example, based on a distance of the retail location to the current location of the vehicle, a travel time associated with the retail location, or based on a frustration level of the vehicle occupant. The monetary incentive may include an amount of currency or a coupon redeemable at the retail location.

Figure 10:
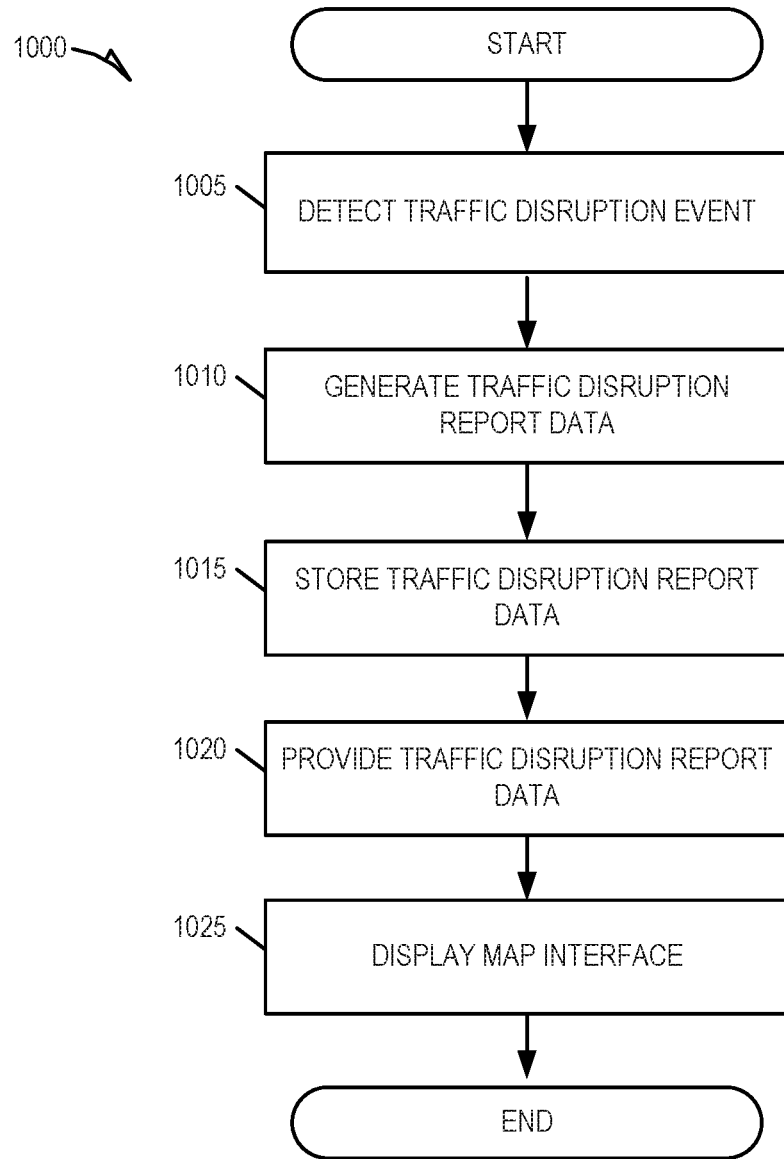
FIG. 10 is a flow chart illustrating a method for reporting a traffic disruption event based on vehicle occupant frustration level, according to an example embodiment.

FIG. 10 is a flow chart illustrating a method for reporting a traffic disruption event based on vehicle occupant frustration level, according to an example embodiment. The method 1000 may be embodied in computer-readable instructions for execution by one or more processors such that the steps of the method 1000 may be performed in part or in whole by functional components (e.g., modules) of a mobile device 106 or the navigation server 110; accordingly, the method 1000 is described below by way of example with reference thereto. However, it shall be appreciated that the method 1000 may be deployed on various other hardware configurations and is not intended to be limited to the functional components of the mobile device 106 or the navigation server 110.

At operation 1005, the event detection module 208 detects a traffic disruption event at a particular location based on frustration scores associated with vehicles within a predefined distance of the particular location. The traffic disruption event may be one of several types of traffic disruption events including for example, accidents, construction road closures, police and speed traps, or a road hazard. The predefined distance may be set by an administrator of the navigation system 100. The frustration scores associated with each vehicle may be determined based on input component data obtained from one or more input components embedded in or coupled to navigation-enabled devices in the vehicles. The navigation-enabled devices may be carried by occupants of the vehicle or included in the vehicle itself, and in this way, the frustration scores associated with each vehicle provide a measure a vehicle occupant's level of frustration. Further details of determining a frustration level of a vehicle occupant are discussed above in reference to FIG. 6, according to some example embodiments. Further details regarding the detection of a traffic disruption event are discussed below in reference to FIG. 12, according to some example embodiments.

At operation 1010, the reporting module 210 generates, in an automated manner without user intervention, traffic disruption report data in response to detecting the traffic disruption event. The traffic disruption report data includes a record of the traffic disruption event, an identifier of the particular location, and a time stamp corresponding to when the traffic disruption event was detected. At operation 1015, the reporting module 210 stores the traffic disruption report data in the database 120.

At operation 1020, the communication module 214 provides the traffic disruption report data to one or more other devices (e.g., mobile devices or servers). For example, the communication module 214 may transmit the traffic disruption data to a third party navigation service (e.g., hosted by third party server 108). As another example, the communication module 214 may transmit one or more traffic disruption event notifications to mobile devices of other users of the navigation system 100 to provide the traffic disruption data thereto. The communication module 214 may transmit the traffic disruption event notification to mobile devices traveling along a route that includes the particular location so as to alert incoming vehicles of the traffic disruption event.

At operation 1025, the interface module 200 causes a display of a user interface on at least one mobile device corresponding to a user of the navigation system 100. The user interface includes a map display of a current location of the mobile device along with an alert or indication of the traffic disruption event at the particular location.

Figure 11:
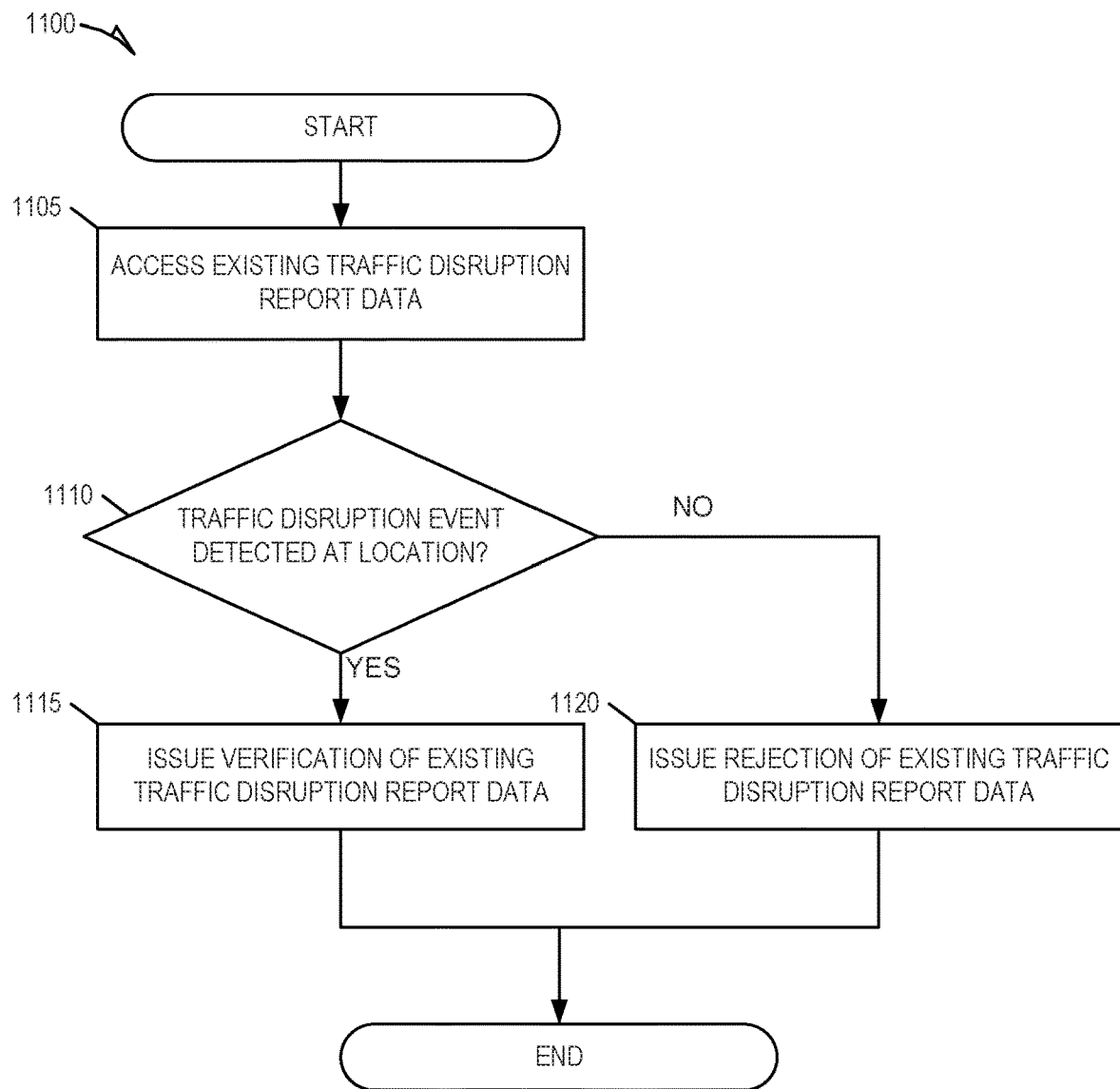
FIG. 11 is a flow chart illustrating a method for verifying an existing traffic disruption report, according to an example embodiment.

FIG. 11 is a flow chart illustrating a method for verifying an existing traffic disruption report, according to an example embodiment. The method 1100 may be embodied in computer-readable instructions for execution by one or more processors such that the steps of the method 1100 may be performed in part or in whole by functional components (e.g., modules) of a mobile device 106 or the navigation server 110; accordingly, the method 1100 is described below by way of example with reference thereto. However, it shall be appreciated that the method 1100 may be deployed on various other hardware configurations and is not intended to be limited to the functional components of the mobile device 106 or the navigation server 110.

At operation 1105, the verification module 212 accesses existing traffic disruption report data corresponding to a particular location. The existing traffic disruption report data may correspond to a user generated traffic disruption report of a traffic disruption event. The existing traffic disruption report data is stored and accessed from the database 120.

At operation 1110, the verification module 212 determines whether a traffic disruption event has been detected at the particular location corresponding to the existing traffic disruption report data based on frustration scores associated with vehicles near the particular location. Further details regarding the detection of a traffic disruption event are discussed below in reference to FIG. 12.

If at operation 1110 the verification module 212 determines that a traffic disruption event has been detected at the particular location, the verification module 212, at operation 1115, issues a verification of the existing traffic disruption report data and the existing traffic disruption report data is maintained in the database 120.

If at operation 1110 the verification module 212 determines that a traffic disruption event has not been detected at the particular location, the verification module 212 at operation 1120 flags the exiting traffic disruption report data as being invalid. The navigation service 104 may delete the existing traffic disruption report data in response to the verification module 212 flagging the existing traffic disruption report data.

Figure 12:
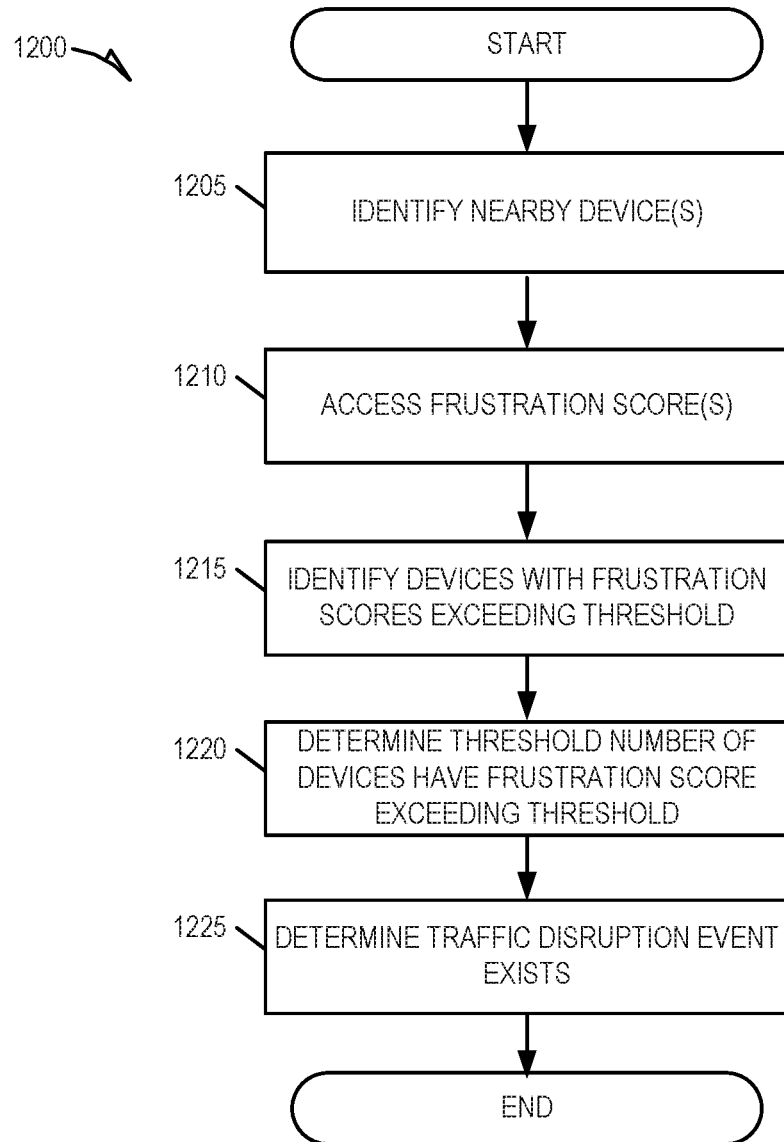
FIG. 12 is a flow chart illustrating a method for detecting a traffic disruption event based on vehicle occupant frustration level, according to an example embodiment.

FIG. 12 is a flow chart illustrating a method 1200 for detecting a traffic disruption event based on vehicle occupant frustration level, according to an example embodiment. The method 1200 may be embodied in computer-readable instructions for execution by one or more processors such that the steps of the method 1200 may be performed in part or in whole by functional components (e.g., modules) of a mobile device 106 or the navigation server 110; accordingly, the method 1200 is described below by way of example with reference thereto. However, it shall be appreciated that the method 1200 may be deployed on various other hardware configurations and is not intended to be limited to the functional components of the mobile device 106 or the navigation server 110.

At operation 1205, the location tracking module 216 identifies one or more vehicles near the particular location. More specifically, the location tracking module 216 identifies navigation-enabled devices within a predefined distance of the particular location. The predefined distance may be set by an administrator of the navigation system 100. The navigation-enabled devices near the particular location may be identified based on location information (e.g., GPS data) obtained from location components (e.g., GPS components) embedded in the mobile devices.

At operation 1210, the event detection module 208 accesses frustration scores associated with each of the nearby navigation-enabled devices determined by the scoring module 222 based on input component data obtained from one or more input components embedded in or coupled to the nearby devices. Further details regarding the determination of frustration scores are discussed above in reference to FIG. 6 according to some example embodiments.

At operation 1215, the analysis module identifies one or more of the nearby devices with frustration scores exceeding a threshold frustration score. The threshold frustration score may be unique to each navigation-enabled device and may be based on emotional baseline data included in a user record of occupants of the vehicle who are using the navigation-enabled devices. In some embodiments, the threshold frustration score is set by an administrator of the navigation system 100.

At operation 1220, the event detection module 208 determines that a threshold number of devices have a frustration score exceeding the frustration score threshold. The threshold number of devices may include or be based on a percentage of nearby devices such that a certain percentage of the nearby devices are identified as having a frustration score exceeding the frustration score threshold. For example, in some embodiments, the event detection module 208 may, at operation 1220, determine that a majority of the nearby devices have a frustration score that exceeds the frustration score threshold. It shall be noted that the threshold number of nearby devices having the frustration score exceeding the threshold frustration score is not limited to a majority and may in other embodiments include other percentages that may be a minority of devices.

At operation 1225, the event detection module 208 determines a traffic disruption event exists at the particular location based on determining that a threshold number of devices have a frustration score exceeding the frustration score threshold.

Figure 13A:
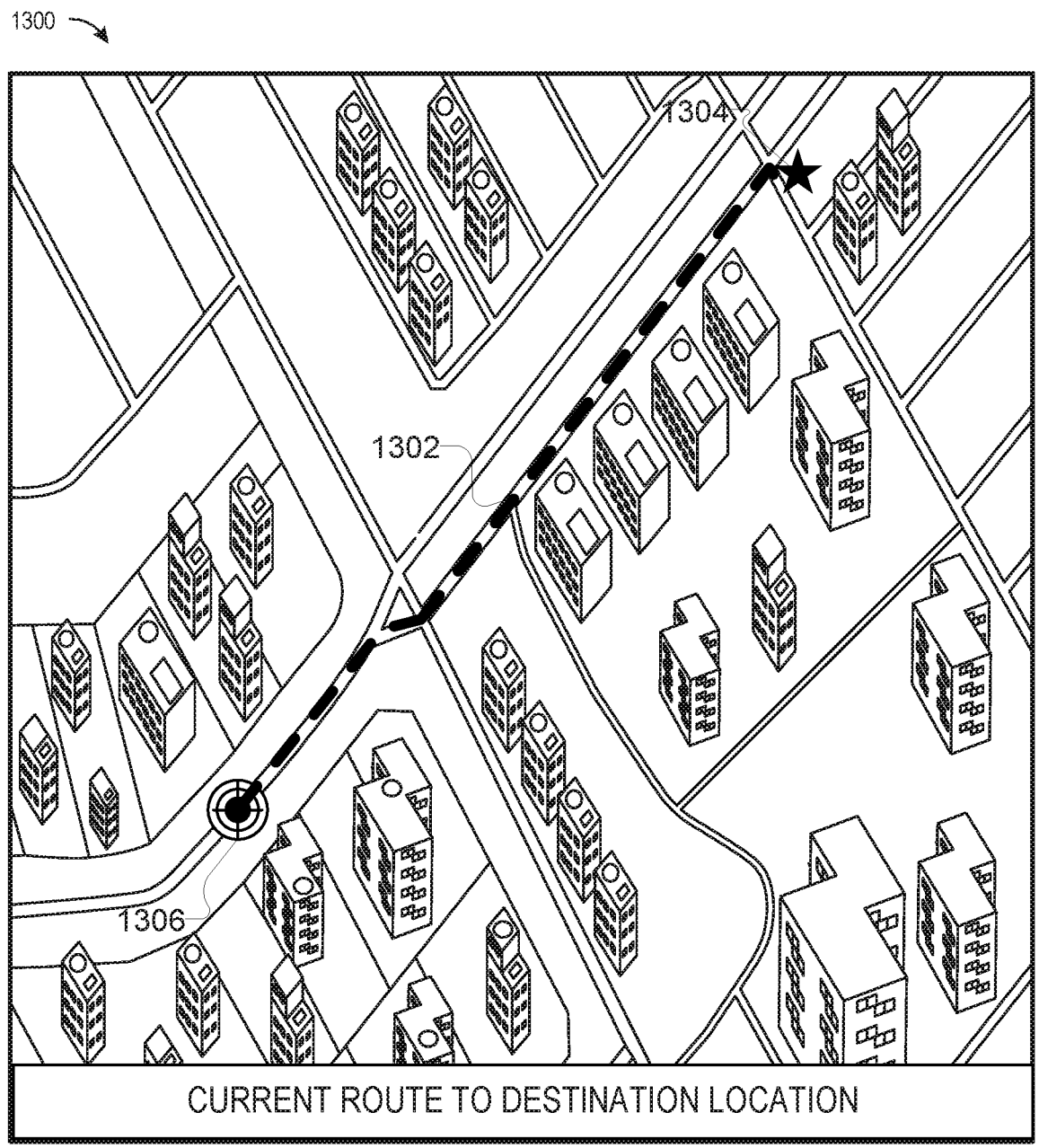
FIG. 13A is an interface diagram illustrating a user interface displaying a current route to a destination location, according to an example embodiment.

FIG. 13A is an interface diagram illustrating a user interface 1300 displaying a current route 1302 to a destination location 1304, according to an example embodiment.

The user interface 1300 may, for example, be presented on a navigation-enabled device such as the mobile device 106. As shown, the user interface 1300 includes a map display of an area surrounding and including a current location 1306 of a vehicle. The map display also includes the current route 1302 of the vehicle to the destination location 1304. The current location 1306 of the vehicle is determined by the location tracking module 216 based on location information (e.g., GPS data) received from a location component (e.g., a GPS component) embedded in a navigation device (e.g., mobile device 106) located in the vehicle (e.g., carried by an occupant of the vehicle or included as a built-in component of the vehicle). In some instances, the current route 1302 of the vehicle may be one of several routes determined by the routing engine 202 from a starting location of the vehicle to the user selected destination location 1304 and selected by a user of the navigation device. In other instances, the current route 1302 and destination location 1304 may be inferred by the routing engine 202 based on a combination of location information (e.g., GPS data) and calendar data (e.g., a calendar event) obtained from the navigation device. In still other instances, the current route 1302 and destination location 1304 may be inferred by the routing engine 202 based on a combination of location information (e.g., GPS data) obtained from the navigation device and a location history stored in a user account record maintained in the database 120.

Figure 13B:
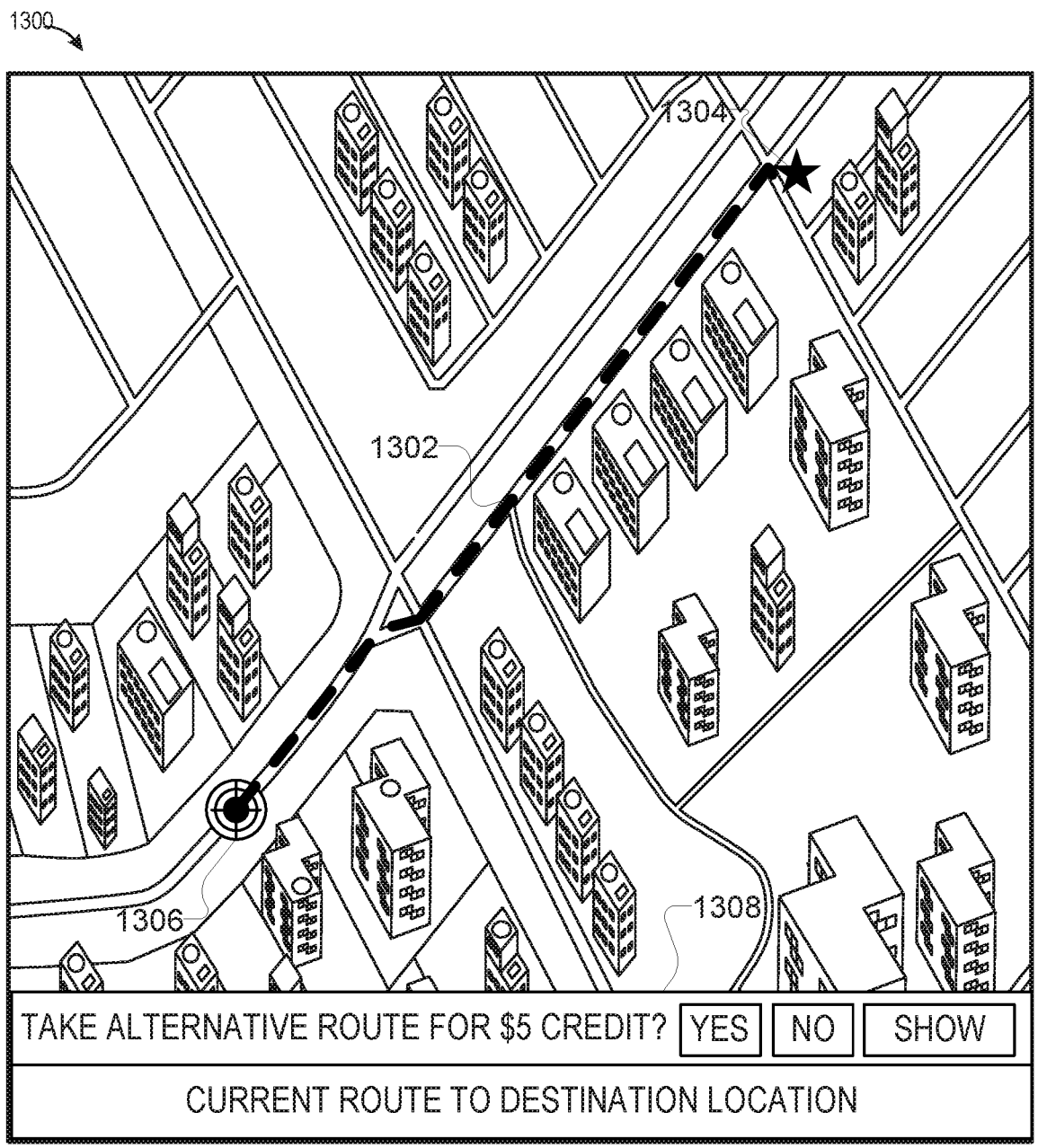
FIG. 13B is an interface diagram illustrating the user interface updated to display an alternative route notification, according to an example embodiment.

FIG. 13B is an interface diagram illustrating the user interface 1300 updated to display an alternative route notification 1308, according to an example embodiment. In some embodiments, the alternative route notification 1308 may be displayed in response to the re-routing module 204 determining that the current route 1302 to the destination location 1304 is a primary route to the destination location 1304. For example, the re-routing module 204 may determine that the current route 1302 is a primary route based on determining that, of the multiple possible routes from the current location 1306 of the vehicle to the destination location 1304, the current route 1302 has the shortest associated travel time (e.g., based on a combination of a length of the route and traffic information along the route).

In other embodiments, the alternative route notification 1308 may be displayed in response to the data analysis module 206 determining that a frustration score associated with the vehicle (e.g., determined based on input component data received from input components associated with the navigation device in the vehicle) is above a threshold. In this way, the alternative route notification 1308 is provided in an effort to reduce the current frustration score associated with the vehicle, which may be caused by traffic conditions along the current route 1302.

In FIG. 13B, the alternative route notification 1308 is displayed in conjunction with the map display, although the alternative route notification 1308 is not limited to such a manner of display, and may, in other embodiments, be displayed in another manner such as in a separate interface or window or as a push notification. The alternative route notification 1308 includes interactive elements (e.g., buttons) that allow a user, through appropriate input or manipulation, to decline travel on the alternative route (displayed as a "NO" button), accept travel on the alternative route (displayed as a "YES" button), or view the alternative route on the map display (displayed as a "SHOW" button). If the user selects the "NO" button, no further action is taken and the vehicle continues along the current route 1302 (either through action of a driver in a manned vehicle or in an automated process performed by an onboard computer system embedded in an autonomous vehicle). If the user selects the "YES" button or if the vehicle is determined to be traveling along the alternative route (e.g., based on location information obtained from the navigation device), the incentive module 220 updates the user account record of a vehicle occupant to reflect an increase in account balance based on participation in the rerouting service, and also updates the user account records of occupants of other vehicles traveling along the current route 1302 to reflect a decrease in account balance.

Figure 13C:
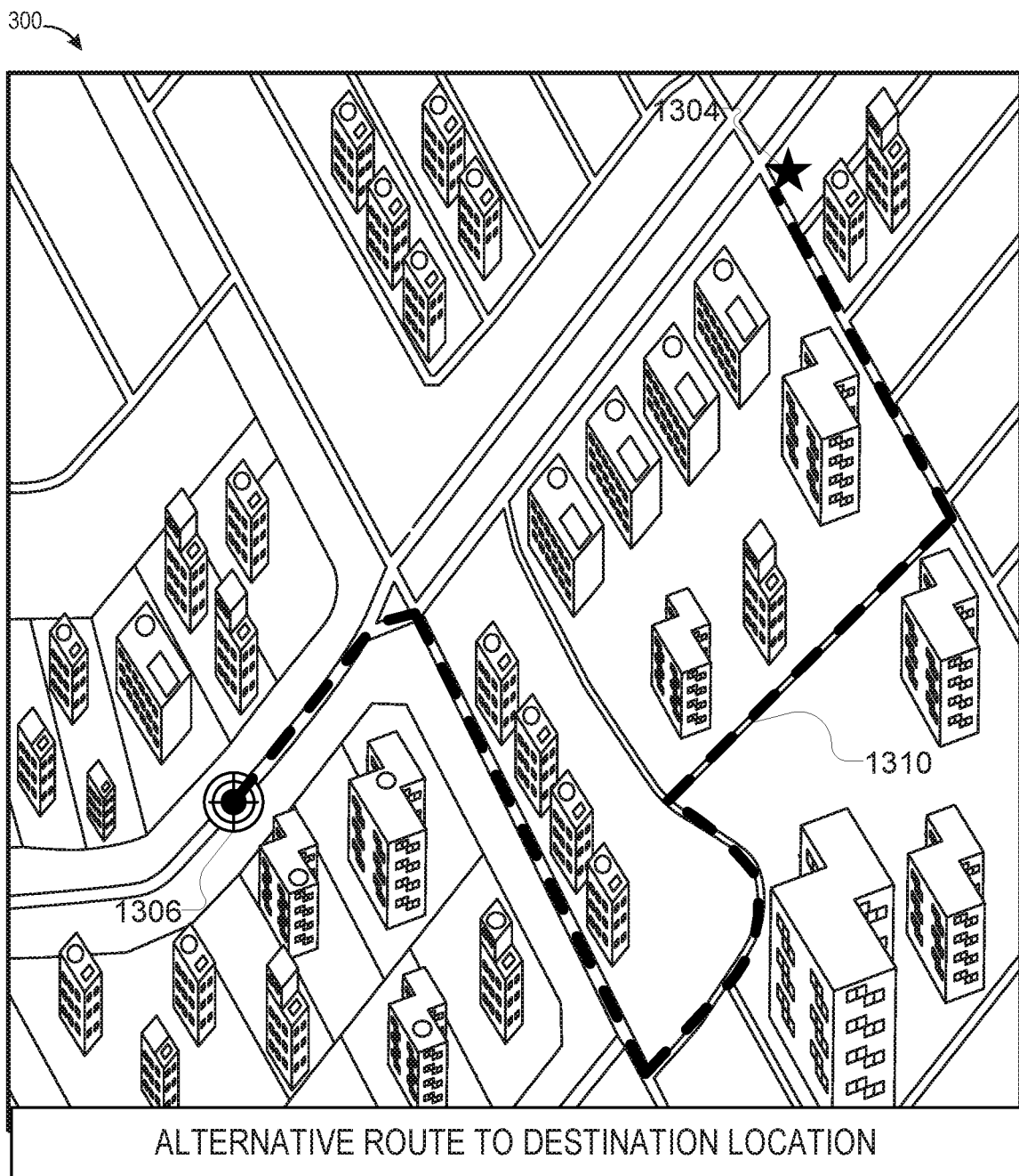
FIG. 13C is an interface diagram illustrating the user interface that has been further updated to display the suggested alternative route, according to an example embodiment.

In response to the user selecting the "SHOW" button, the user interface 1300 is further updated to display the suggested alternative route, as illustrated in FIG. 13C. As shown in FIG. 13C, the map display of the user interface 1300 has been updated to display alternative route 1310. The alternative route 1310 is a path from the current location 1306 of the vehicle to the destination location 1304 that is different than the current route 1302. The alternative route 1310 may be selected by the re-routing module 204 from among a plurality of routes to the destination location 1304 from the current location 1306 of the vehicle determined by the routing engine 202 based on entries in a user preferences field of a user account record (e.g., user account record 300) of an occupant of the vehicle. In particular, the alternative route 1310 may be selected based on an allowable travel time deviation or a total travel time specified by the user and included as an entry in the user preferences field of the user account record.

FIG. 14A is an interface diagram illustrating a user interface 1400 displaying a current location 1402 of a vehicle and a detour suggestion 1404 for an alternative destination, according to an example embodiment. The user interface 1400 may, for example, be presented on a navigation-enabled device such as the mobile device 106. As shown, the user interface 1400 includes a map display of an area surrounding and including a current location 1402 of a vehicle. The current location 1402 of the vehicle is determined by the location tracking module 216 based on location information (e.g., GPS data) received from a location component (e.g., a GPS component) embedded in a navigation-enabled device (e.g., mobile device 106) located in the vehicle (e.g., carried by an occupant of the vehicle or included as a built-in component of the vehicle).

In FIG. 14A, the detour suggestion 1404 is displayed in conjunction with the map display of the user interface 1400, though the detour suggestion 1404 is not limited to such a manner of display, and may, in other embodiments, be displayed in another manner such as in a separate interface or window or as a push notification. The detour suggestion 1404 is presented in the user interface 1400 in response to determining a frustration score associated with the vehicle (e.g., a frustration score associated with a user of a navigation-enabled device in the vehicle) is above a threshold. The detour suggestion 1404 includes interactive elements (e.g., buttons) that allow a user, through appropriate input or manipulation, to decline travel to the alternative destination (displayed as a "DECLINE" button), accept travel to the alternative destination (displayed as a "ACCEPT" button), or view the detour route to the alternative destination on the map display (displayed as a "SHOW DETOUR ROUTE" button). If the user selects the "DECLINE" button, no further action is taken and the vehicle continues along the current route 1402 (either through action of a driver in a manned vehicle or in an automated process performed by an onboard computer system embedded in an autonomous vehicle). If the user selects the "ACCEPT" button, an incentive (e.g., a coupon) is provided to the user, and the vehicle is routed to the alternative destination (either through action of a driver in a manned vehicle or in an automated process performed by an onboard computer system embedded in an autonomous vehicle in response to selection of the button). In response to the user selecting the "SHOW DETOUR ROUTE" button, the user interface 1400 is further updated to display the detour route to the alternative destination, as illustrated in FIG. 14B. As illustrated in FIG. 14B, the updated user interface 1400 includes a detour route 1406 to an alternative destination 1408. The detour route 1406 may be determined by the routing engine 202 based on a travel time associated with the route. For example, the routing engine 202 may select the route from the current location of the vehicle 1402 to the alternative destination 1408 with the shortest associated travel time. In some embodiments, the alternative destination 1408 is selected based on information included in a user account record of an occupant in the vehicle. For example, the alternative destination 1408 may be selected based on user preferences (e.g., a brick-and-mortar retail location selected within an allowable distance of the current location of the vehicle specified by the user), from a location history of the user (e.g., a location previously traveled to by the user), or from a transaction history of the user (e.g., a location from which the user previously purchased an item). While the alternative destination 1408 illustrated in FIG. 14B corresponds to a brick-and-mortar retail location, alternative destinations included in detour suggestions are not necessarily limited to such locations.

Machine Architecture

Figure 15:
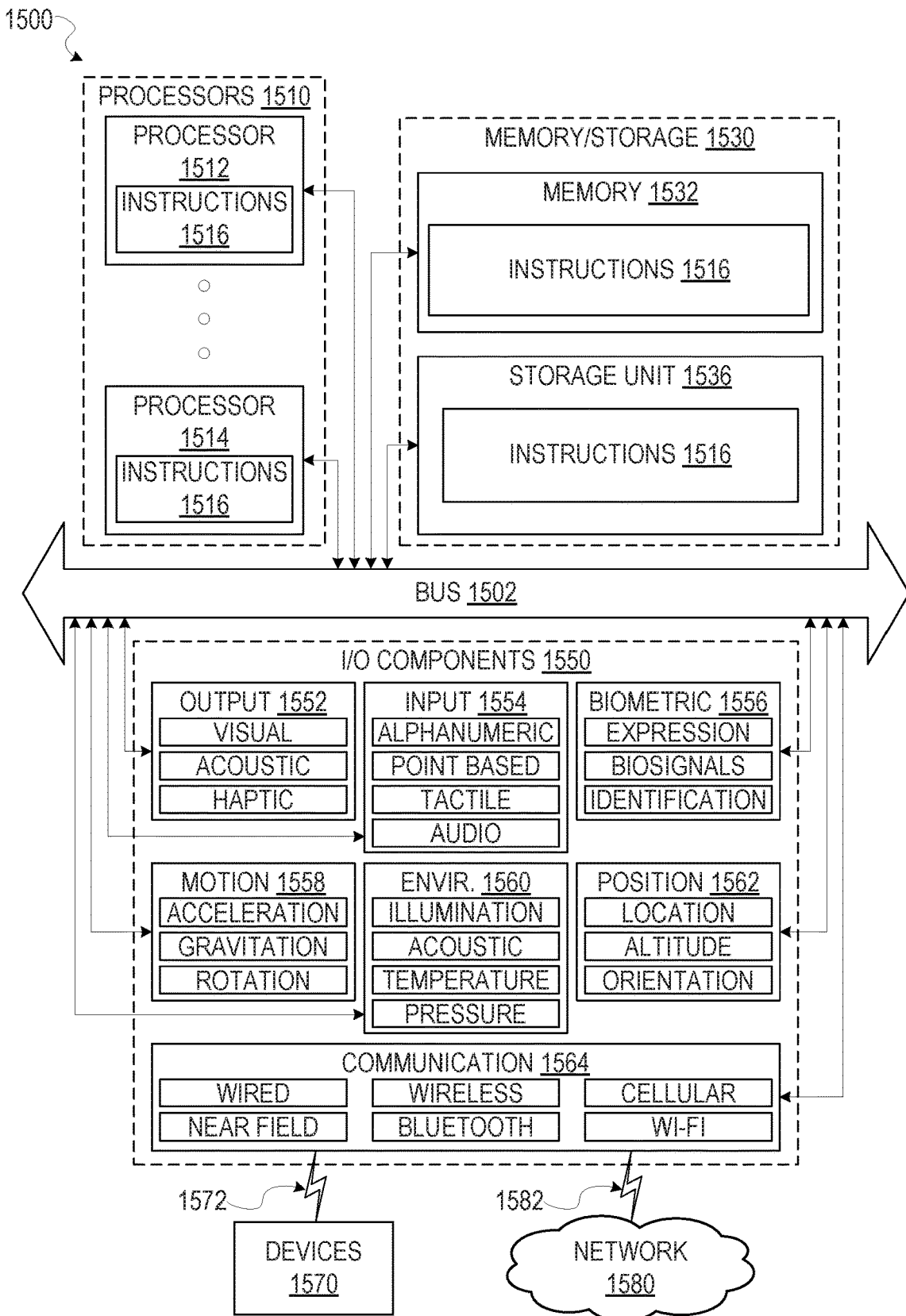
FIG. 15 is a diagrammatic representation of a machine in the example form of a computer system within which a set of instructions for causing the machine to perform any one or more of the methodologies discussed herein may be executed.

FIG. 15 is a block diagram illustrating components of a machine 1500, according to some example embodiments, able to read instructions from a machine-readable medium (e.g., a machine-readable storage medium) and perform any one or more of the methodologies discussed herein. Specifically, FIG. 15 shows a diagrammatic representation of the machine 1500 in the example form of a computer system, within which instructions 1516 (e.g., software, a program, an application, an applet, an app, or other executable code) for causing the machine 1500 to perform any one or more of the methodologies discussed herein may be executed. These instructions transform the general, non-programmed machine into a specially configured machine programmed to carry out the described and illustrated functions described herein. Consistent with some embodiments, the machine 1500 may correspond to the mobile device 106 or the navigation server 110.

The machine 1500 may operate as a standalone device or may be coupled (e.g., networked) to other machines. In a networked deployment, the machine 1500 may operate in the capacity of a server machine or a client machine in a server-client network environment, or as a peer machine in a peer-to-peer (or distributed) network environment. By way of non-limiting example, the machine 1500 may comprise or correspond to a server computer, a client computer, a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 1516, sequentially or otherwise, that specify actions to be taken by machine 1500. Further, while only a single machine 1500 is illustrated, the term "machine" shall also be taken to include a collection of machines 1500 that individually or jointly execute the instructions 1516 to perform any one or more of the methodologies discussed herein.

The machine 1500 may include processors, memory 1530, and input and output (I/O) components 1550, which may be configured to communicate with each other such as via a bus 1502. In an example embodiment, the processors 1510 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuit (ASIC), a Radio-Frequency Integrated Circuit (RFIC), another processor, or any suitable combination thereof) may include, for example, processor 1512 and processor 1514 that may execute instructions 1516. The term "processor" is intended to include multi-core processor that may comprise two or more independent processors (sometimes referred to as "cores") that may execute instructions contemporaneously. Although FIG. 15 shows multiple processors, the machine 1500 may include a single processor with a single core, a single processor with multiple cores (e.g., a multi-core process), multiple processors with a single core, multiple processors with multiples cores, or any combination thereof.

The memory/storage 1530 may include a memory 1532, such as a main memory, or other memory storage, and a storage unit 1536, both accessible to the processors 1510 such as via the bus 1502. The storage unit 1536 and memory 1532 store the instructions 1516 embodying any one or more of the methodologies or functions described herein. The instructions 1516 may also reside, completely or partially, within the memory 1532, within the storage unit 1536, within at least one of the processors 1510 (e.g., within the processor's cache memory), or any suitable combination thereof, during execution thereof by the machine 1000. Accordingly, the memory 1532, the storage unit 1536, and the memory of processors 1510 are examples of machine-readable media.

As used herein, "machine-readable medium" means a device able to store instructions and data temporarily or permanently and may include, but is not be limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions 1016. The term "machine-readable medium" shall also be taken to include any medium, or combination of multiple media, that is capable of storing instructions (e.g., instructions 1516) for execution by a machine (e.g., machine 1500), such that the instructions, when executed by one or more processors of the machine 1500 (e.g., processors 1510), cause the machine 1500 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The I/O components 1550 may include a wide variety of components to receive input, provide output, produce output, transmit information, exchange information, capture measurements, and so on. The specific I/O components 1550 that are included in a particular machine will depend on the type of machine. For example, portable machines such as mobile phones will likely include a touch input device or other such input mechanisms, while a headless server machine will likely not include such a touch input device. It will be appreciated that the I/O components 1550 may include many other components that are not shown in FIG. 15. The I/O components 1550 are grouped according to functionality merely for simplifying the following discussion and the grouping is in no way limiting. In various example embodiments, the I/O components 1550 may include output components 1552 and input components 1554. The output components 1552 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 1554 may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 1550 may include biometric components 1556, motion components 1558, environmental components 1560, or position components 1562, among a wide array of other components. For example, the biometric components 1556 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 1558 may include acceleration sensor components (e.g., accelerometer), gravitation sensor components, rotation sensor components (e.g., gyroscope), and so forth. The environmental components 1560 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 1562 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 1550 may include communication components 1564 operable to couple the machine 1500 to a network 1580 or devices 1570 via coupling 1582 and coupling 1572, respectively. For example, the communication components 1564 may include a network interface component or other suitable device to interface with the network 1580. In further examples, communication components 1564 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 1570 may be another machine or any of a wide variety of peripheral devices (e.g., a peripheral device coupled via a Universal Serial Bus (USB)).

Moreover, the communication components 1564 may detect identifiers or include components operable to detect identifiers. For example, the communication components 1564 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 1564, such as location via Internet Protocol (IP) geo-location, location via Wi-Fi® signal triangulation, location via detecting a NFC beacon signal that may indicate a particular location, and so forth.

Transmission Medium

In various example embodiments, one or more portions of the network 1580 may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, the network 1580 or a portion of the network 1580 may include a wireless or cellular network and the coupling 1582 may be a Code Division Multiple Access (CDMA) connection, a Global System for Mobile communications (GSM) connection, or other type of cellular or wireless coupling. In this example, the coupling 1582 may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

The instructions 1516 may be transmitted or received over the network 1580 using a transmission medium via a network interface device (e.g., a network interface component included in the communication components 1564) and utilizing any one of a number of well-known transfer protocols (e.g., hypertext transfer protocol (HTTP)). Similarly, the instructions 1516 may be transmitted or received using a transmission medium via the coupling 1572 (e.g., a peerto-peer coupling) to devices 1570. The term "transmission medium" shall be taken to include any intangible medium that is capable of storing, encoding, or carrying instructions 1516 for execution by the machine 1500, and includes digital or analog communications signals or other intangible medium to facilitate communication of such software.

Modules, Components and Logic

Certain embodiments are described herein as including logic or a number of components, modules, or mechanisms. Modules may constitute either software modules (e.g., code embodied on a machine-readable medium or in a transmission signal) or hardware modules. A hardware module is a tangible unit capable of performing certain operations and may be configured or arranged in a certain manner. In example embodiments, one or more computer systems (e.g., a standalone, client, or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field-programmable gate array (FPGA) or an ASIC) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses that connect the hardware modules). In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment, or a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., APIs).

Electronic Apparatus and System

Example embodiments may be implemented in digital electronic circuitry, or in computer hardware, firmware, or software, or in combinations of them. Example embodiments may be implemented using a computer program product, for example, a computer program tangibly embodied in an information carrier, for example, in a machine-readable medium for execution by, or to control the operation of, data processing apparatus, for example, a programmable processor, a computer, or multiple computers.

A computer program can be written in any form of programming language, including compiled or interpreted languages, and it can be deployed in any form, including as a standalone program or as a module, subroutine, or other unit suitable for use in a computing environment. A computer program can be deployed to be executed on one computer or on multiple computers at one site, or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry (e.g., an FPGA or an ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that both hardware and software architectures merit consideration. Specifically, it will be appreciated that the choice of whether to implement certain functionality in permanently configured hardware (e.g., an ASIC), in temporarily configured hardware (e.g., a combination of software and a programmable processor), or in a combination of permanently and temporarily configured hardware may be a design choice. Below are set out hardware (e.g., machine) and software architectures that may be deployed, in various example embodiments.

Although the embodiments of the present invention have been described with reference to specific example embodiments, it will be evident that various modifications and changes may be made to these embodiments without departing from the broader scope of the inventive subject matter. Accordingly, the specification and drawings are to be regarded in an illustrative rather than a restrictive sense. The accompanying drawings that form a part hereof show by way of illustration, and not of limitation, specific embodiments in which the subject matter may be practiced. The embodiments illustrated are described in sufficient detail to enable those skilled in the art to practice the teachings disclosed herein. Other embodiments may be used and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent, to those of skill in the art, upon reviewing the above description.

All publications, patents, and patent documents referred to in this document are incorporated by reference herein in their entirety, as though individually incorporated by reference. In the event of inconsistent usages between this document and those documents so incorporated by reference, the usage in the incorporated references should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended; that is, a system, device, article, or process that includes elements in addition to those listed after such a term in a claim are still deemed to fall within the scope of that claim.

What is claimed is:

1. A method comprising:
    detecting a traffic disruption event at a particular location;
    obtaining sensor data from a plurality of devices, the sensor data captured by respective sensors associated with the plurality of devices;
    determining, based on the sensor data, a measure of frustration associated with one or more of the plurality of devices within a threshold distance of a location of the traffic disruption event; and
    verifying the traffic disruption event based on the determined measure of frustration.

2. The method of claim 1, wherein the verifying the traffic disruption event includes comparing the particular location of the traffic disruption event to location data received with the sensor data obtained from the plurality of devices.

3. The method of claim 1, wherein the determining the measure of frustration includes comparing the sensor data to baseline data stored in user account records maintained in a database.

4. The method of claim 1, further comprising transmitting a verification of the traffic disruption event to one or more of the plurality of devices.

5. The method of claim 1, further comprising causing display of a map within a user interface, the map including an indicator of the traffic disruption event.

6. The method of claim 1, wherein the sensor data includes motion data obtained from respective motion sensors associated with the plurality of devices.

7. The method of claim 6, wherein the determining the measure of frustration includes determining a velocity or frequency of motion of one or more of the plurality of devices from the motion data.

8. The method of claim 1, wherein the sensor data includes heart rate data obtained from respective heart rate sensors associated with the plurality of devices.

9. The method of claim 8, wherein the determining the measure of frustration includes:
    determining a heart rate of at least one user associated with at least one of the plurality of devices based on heart rate data; and
    comparing the determined heart rate to baseline heart data included in a user account record of the user.

10. The method of claim 1, wherein the sensor data includes audio data obtained from a microphone, and wherein the determining the measure of frustration includes determining an audio level of the audio data.

11. The method of claim 10, wherein the determining the measure of frustration further includes:
    identifying, from the audio data, one or more keywords using speech recognition; and
    comparing the one or more keywords to a repository of frustration terms.

12. The method of claim 1, wherein each of the plurality of devices are associated with respective users traveling in a vehicle.

13. The method of claim 1, wherein the verifying comprising determining that at least one of the devices is within a predefined distance of the particular location have an associated measure of frustration above a predefined threshold.

14. A non-transitory machine-readable storage medium embodying instructions that, when executed by a machine, cause the machine to perform operations comprising:
- detecting a traffic disruption event at a particular location;
- obtaining sensor data from a plurality of devices, the sensor data captured by respective sensors associated with the plurality of devices;
- determining, based on the sensor data, a measure of frustration associated with one or more of the plurality of devices within a threshold distance of a location of the traffic disruption event; and
- verifying the traffic disruption event based on the determined measure of frustration.

15. The non-transitory machine-readable storage medium of claim 14, wherein the verifying the traffic disruption event includes comparing the particular location of the traffic disruption event to location data received with the sensor data obtained from the plurality of devices.

16. The non-transitory machine-readable storage medium of claim 14, wherein the determining the measure of frustration includes comparing the sensor data to baseline data stored in user account records maintained in a database.

17. The non-transitory machine-readable storage medium of claim 14, wherein the operations further comprise transmitting a verification of the traffic disruption event to one or more of the plurality of devices.

18. The non-transitory machine-readable storage medium of claim 14, wherein the sensor data includes motion data obtained from respective motion sensors associated with the plurality of devices.

19. The non-transitory machine-readable storage medium of claim 18, wherein the determining the measure of frustration includes determining a velocity or frequency of motion of one or more of the plurality of devices from the motion data.

20. A system comprising:
- one or more processors of a machine; and
- one or more machine-readable mediums storing instructions to configure the one or more processors to perform operations comprising:
  - detecting a traffic disruption event at a particular location;
  - obtaining sensor data from a plurality of devices, the sensor data captured by respective sensors associated with the plurality of devices;
  - determining, based on the sensor data, a measure of frustration associated with one or more of the plurality of devices within a threshold distance of a location of the traffic disruption event; and
  - verifying the traffic disruption event based on the determined measure of frustration.

* * * * *